United States Patent [19]

Albaugh

[11] Patent Number: 5,264,449
[45] Date of Patent: Nov. 23, 1993

[54] N-SUBSTITUTED DERIVATIVES OF 3R,4R-ETHYL-[(1-METHYL-1H-IMIDAZOL-5-YL)METHYL]-2-PYRROLIDINONE

[75] Inventor: Pamela Albaugh, Clinton, Conn.

[73] Assignee: Allergan, Inc., Irvine, Calif.

[21] Appl. No.: 434,929

[22] Filed: Nov. 13, 1989

[51] Int. Cl.$^5$ .................. A61K 31/415; C07D 403/00
[52] U.S. Cl. .................... 514/397; 548/110; 548/314.7
[58] Field of Search ................ 548/336, 110; 514/397

[56] References Cited

U.S. PATENT DOCUMENTS 3,470,197  9/1969  Van Dyke ..................... 548/336

OTHER PUBLICATIONS

J. Pharm. Sci., 62, 2021 (1973).

*Primary Examiner*—Mary C. Lee
*Assistant Examiner*—Robert C. Whittenbaugh
*Attorney, Agent, or Firm*—Knobbe, Martens, Olson & Bear

[57] ABSTRACT

The present invention relates to new carbonyl 3R, 4R-ethyl-[(1-methyl-1H-imidazol-5-yl) methyl]-2-pyrrolidinone derivatives carrying a carboxyester-type lipophilic moiety on the pyrrolidinone nitrogen. More particularly, the present invention concerns new N-substituted carbonyl-3R,4R-ethyl-[(1-methyl-1H-imidazol-5-yl) methyl]-2-pyrrolidinone derivatives of the formula (I):

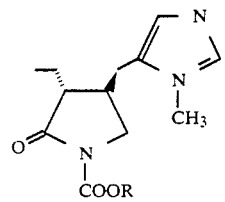

wherein R is an optionally substituted hydrocarbon group, and pharmaceutically acceptable acid addition salts thereof.

The new compounds of the formula (I) are potent ocular hypotensives that are valuable antiglaucoma agents. They are also targeted for use in the treatment of so-called dry eye.

4 Claims, 3 Drawing Sheets

N-SUBSTITUTED DERIVATIVES OF 3R,4R-ETHYL-[(1-METHYL-1H-IMIDAZOL-5-YL)METHYL]-2-PYRROLIDINONE

FIELD OF THE INVENTION

The present invention relates to new chemical compounds having valuable pharmacological properties. More particularly, the present invention concerns novel, pharmaceutically active N-substituted derivatives of 3R,4R-ethyl-[(1-methyl-1H-imidazol-5-yl) methyl]-2-pyrrolidinone.

BACKGROUND OF THE INVENTION

The parent compound used in the preparation of the compounds according to the present invention, 3R,4R-ethyl-[(1-methyl-1H-imidazol-5-yl) methyl]-2-pyrrolidinone, is known in the art, and, together with other 1-alkyl substituted derivatives of the same basic structure, is disclosed in the U.S. Pat. No. 3,470,197. There, it and certain derivatives are described as useful as antiglaucoma agents. Koda, et al., *J. Pharm. Sciences*, 62, 2021 (1973) describes certain of the compounds of U.S. Pat. No. 3,470,197 as possessing cholinergic activity.

Structurally, the parent compound is related to the corresponding lactone, from which it can be prepared. The lactone is a known antiglaucoma agent: 3S,4R-3-ethyl-4-[(1-methyl-1H-imidazol-5-yl) methyl]-3,4-dihydro-2(3H)-furanone (pilocarpine). Both compounds lower intraocular pressure via contraction of the ciliary muscle, and also cause simultaneous contraction of the iris muscle leading to decrease in pupil diameter (miosis) in the patient's eye following topical administration. Pilocarpine is an optically active (3S,4R) compound that is stereoisomeric with isopilocarpine, the optically active trans-isomer (3R,4R). Although pilocarpine is one of the commonly used outflow enhancing drugs used for glaucoma therapy, its use is limited because of its short duration. Our major objective has been to develop pilocarpine analogues with increased duration of action and improved corneal penetration over pilocarpine.

SUMMARY OF THE INVENTION

The present invention relates to new carbonyl 3R,4R-ethyl-[(1-methyl-1H-imidazol-5-yl) methyl]-2-pyrrolidinone derivatives carrying a carboxyester-type lipophilic moiety on the pyrrolidinone nitrogen. More particularly, the present invention concerns new N-substituted carbonyl-3R,4R-ethyl-[(1-methyl-1H-imidazol-5-yl) methyl]-2-pyrrolidinone derivatives of the formula (I):

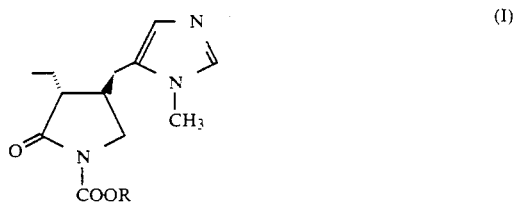

wherein R is an optionally substituted hydrocarbon group, and pharmaceutically acceptable acid addition salts thereof.

In another aspect, the present invention relates to a process for the preparation of the compounds of formula (I), wherein R is hereinabove defined, or pharmaceutically acceptable acid addition salts thereof, by reacting a racemic or optically active compound of the formula (II):

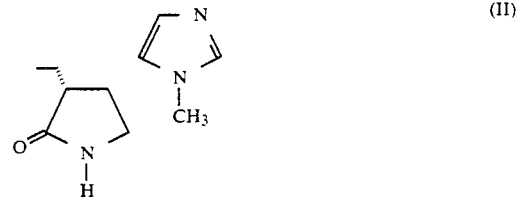

or an acid addition salt thereof, with an appropriate N-acylating agent. If desired, the obtained compounds can be converted into their pharmaceutically acceptable salts, or freed from the obtained acid addition salts. If a racemic starting compound is employed, compounds of the formula (I) are obtained as racemates that can be resolved into the respective enantiomers by methods known in the art. [Jacques, J.; Collet, A.; Wileu, S. H. "Enantiomers, Racemates and Resolutions"; Wiley, N.Y. 1981.]

The new compounds of the formula (I) are potent ocular hypotensives that are valuable antiglaucoma agents. They are also targeted for use in the treatment of so-called dry eye, and demonstrate greater topical activity over the parent compound. Accordingly, in a further aspect, the present invention relates to pharmaceutical compositions containing these compounds or their pharmaceutically acceptable salts, as active ingredients.

DETAILED DESCRIPTION OF THE INVENTION

Figure 1A:
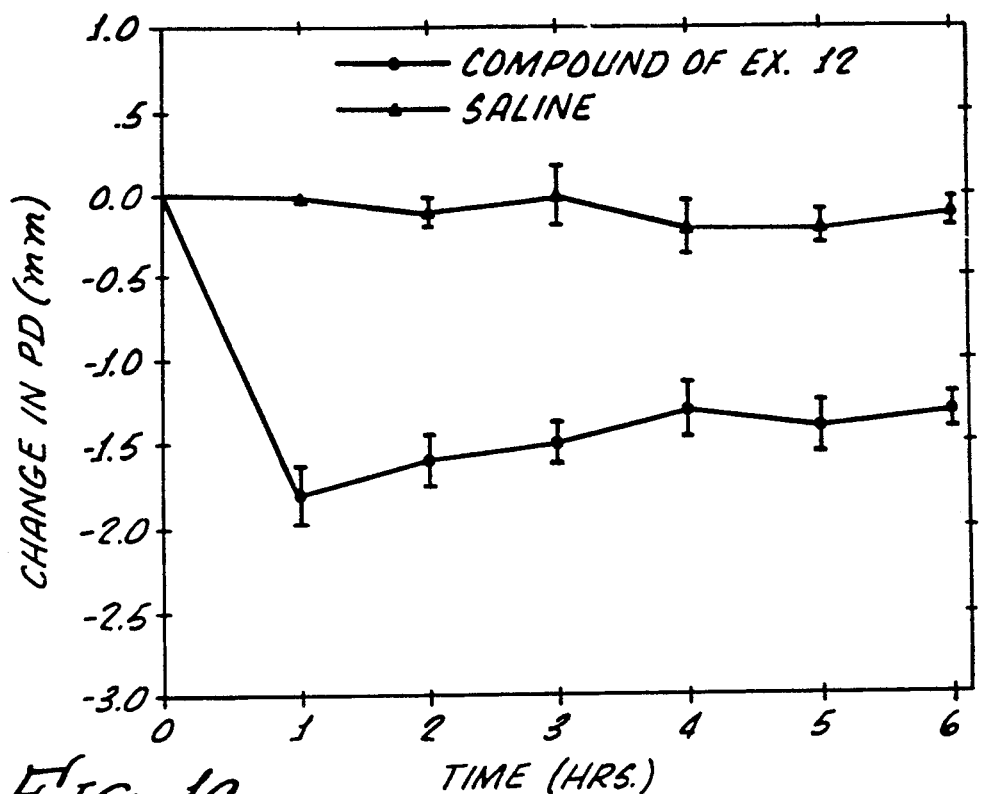
FIG. 1a shows the effect of a 1% solution of the compound of Example 12 on pupil diameter in rabbits.

The starting compound in the synthesis of the compounds of formula (I) (R is as hereinabove defined) is 3R,4R-ethyl-[(1-methyl-1H-imidazol-5-yl)methyl]-2-pyrrolidinone [formula (II)], that can be prepared by reaction of pilocarpine with ammonia in a suitable solvent inert under the reaction conditions, as described in the U.S. Pat. No. 3,470,197. The preferred solvent is ammonia itself. The reaction is a single step reaction and is conveniently performed in an autoclave or high pressure reactor.

According to the invention, a racemic or optically active compound of formula (II) or an acid addition salt thereof, is N-acylated to obtain the desired N-substituted derivatives hereof of the formula (I).

Preferably, a compound of the formula (II) is reacted with a halo- or cyanoformate derivative of the formula (III):

$$XCO_2R \qquad (III)$$

or with an anhydride of the formula (IV):

$$R'O_2COCO_2R \qquad (IV)$$

wherein R is as hereinabove defined,

X is halogen or a cyano group, and

R' is an optionally substituted hydrocarbon group that is identical with or different from R' both in the presence of a base.

Alternatively, the acylation of the compounds of formula (II) may be performed with suitable active esters or carbonates, such as the O-p-nitrophenyl carbonates of the formula (V):

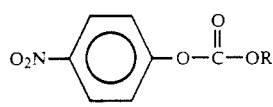

wherein R has the same meaning as hereinabove defined.

In the above formulas, R as a hydrocarbon group may be aliphatic, alicyclic or aromatic. The aliphatic hydrocarbon groups may be straight or branched chained, saturated or unsaturated, such as straight or branched chained alkyl, alkenyl or alkynyl groups, usually containing up to about 20 carbon atoms. Typical representatives of the alkyl groups include, for example, methyl, ethyl, U- and isopropyl, D-, sec-, iso- and tert-butyl, and isopentyl, and neo-hexyl, D- and isoheptyl, U- and iso-octyl, etc. groups. Since the N-substituent on the pyrrolidinone ring in the compounds of formula (I) is desirably a lipophilic moiety, longer, preferably branched chained R alkyl groups are preferred. Typical alkenyl and alkynyl groups are vinyl, allyl, propenyl, crotyl, ethynyl and propargyl.

Alicyclic groups also can be saturated or unsaturated and accordingly, include cycloalkanyl, cycloalkenyl and cycloalkynyl groups such as cyclopropanyl, cyclobutanyl, cyclopentanyl, cyclohexanyl, exo- and endo-norbornyl, etc. groups and the respective cycloalkenyls and cycloalkynls that contain one or more double or triple bonds.

The aromatic hydrocarbon groups (aryl groups) are derived from aromatic hydrocarbons containing one or more six-membered aromatic rings, and include phenyl, α- and β-naphthyl, benzyl, etc.

All of these hydrocarbon groups may carry one or more identical or different substituents that may, for example, be selected from alkyl, alkenyl or alkynyl-, alkoxy, aryloxy, alkoxycarbonyl, hydroxyl, trialkylsilyl and halogen groups. In the substituent definitions, the terms "alkyl," "alkenyl," "alkynyl," "aryl" as such, or as part of other groups, have the same meanings as hereinabove defined.

The term "halogen" is used to include fluorine, chlorine, bromine and iodine, preferably chlorine. Particularly preferred compounds of formula (I) are, for example:

(3R' 4R)-1-carbo-(4-tert-butylbenzoxy)-3-ethyl-4-[(1-methyl -1H-imidazol-5-yl)methyl]-2-pyrrolidinone and (3R' 4R)-1-carbo-(2-propyl-1-pentoxy)-3-ethyl-4-[(1-methyl-1H-imidazol-5-yl) methyl]-2-pyrrolidinone.

If desired, an obtained compound of formula (I), wherein R has the same meanings as defined above, is converted into a pharmaceutically acceptable acid addition salt thereof, or an obtained acid addition salt is converted into the respective free compound or into another pharmaceutically acceptable acid addition salt.

Acid addition salts may be formed with suitable mineral or organic acids, such as hydrochloric acid, hydrobromic acid, sulfuric acid, citric acid, oxalic acid, lactic acid, maleic acid, etc., and can be prepared by methods known per se. The foreseeable requirement is that they be pharmaceutically acceptable for administration to man.

Methods for resolution of racemic compounds of the formula (I) are known in the art, and are disclosed in ordinary textbooks of organic chemistry, such as in Jaques, J.; Collet, A.; Wileu, S. H., suora.

The reaction of the starting compound of formula (II) with the halo- or cyanoformates of the formula (III) or the anhydrides of formula (IV) is performed in a suitable solvent, preferably inert under the reaction conditions. Suitable solvents include, but are not limited to, tetrahydrofuran and dimethylformamide.

The reaction is performed in the presence of a strong base, such as potassium hydride, sodium hydride, lithiodiisopropylamide (that may be prepared by the reaction of diisopropylamine and D-butyl lithium).

Although the reaction temperature is not critical, the reaction is preferably performed at a temperature between about $-100°$ C. and about 50° C., more preferably at about $-78°$ C. or 0° C., depending on the reactants and solvents employed.

Similarly, the acylation with the O-p-nitrophenyl carbonates of the formula (V) is performed in an inert solvent, preferably in the presence of a strong base, such as potassium or sodium hydride, preferably between ambient temperature and 0° C.

The new compounds of the present invention exhibit valuable pharmacological properties. More particularly, these compounds lower intraocular pressure in the eye, and have increased topical activity over the previously described pharmaceutically active, starting compound.

Pharmaceutical compositions may be prepared by combining a therapeutically efficient amount of at least one compound of the formula (I), wherein R is as hereinabove defined, or a pharmaceutically acceptable salt thereof, as an active ingredient, with conventional pharmaceutical excipient. For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives and stabilizers.

Preferred preservatives that may be used in the pharmaceutical compositions of the present invention include, but are not limited to, benzalkonium chloride, chlorobutanol, thimerosal, phenylmercuric acetate and phenylmercuric nitrate.

Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
| --- | --- |
| Muscarinic Agonist | 0.1–5 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| Antioxidant | as needed |
| Purified Water | as needed to make 100% |

A typical ophthalmic preparation of the present invention is illustrated in Example 27.

Further details of the invention are illustrated by the following, non-limiting examples.

EXAMPLE I

Test of Pharmacological Activity

Methods

The test compounds were topically applied in volumes of 25 µl (rabbits) or 10 µl (owl monkeys). Solutions with active ingredient concentrations ranging from 0.5% to 4% were tested. Pupil diameter was measured at times 0, 0.5, 1, 2, 3, 4, 5 and 6 hours after treatment. Normal saline was used as vehicle control, and pilocarpine (0.5–1%) as positive control. Intraocular pressure was also measured at the above times after treatment with selected compounds. Since most of the compounds were oil, they were initially dissolved in 0.01 N acetic acid and brought to the desired final volume with norma saline. The pH of all test solutions was adjusted to 5.

Results

Corneal penetration was determined by measuring miosis following topical application. Effect of the tested compounds of formula (I) on pupil size in rabbits is shown in Table 1.

TABLE 1

| | | | Activity of Isopilocarpine Lactam Compounds on Pupil Size in Pigmented Rabbits | | |
| --- | --- | --- | --- | --- | --- |
| R | EXAMPLE | CONC (%) | DECREASE IN PUPIL DIAM.[a] (mm.) | TIME TO MAX.[b] (hrs.) | DURATION[c] (hrs.) |
| CH$_3$ | 1 | 2 | −0.5 | 0.5 | 6 |
| n-Bu | 2 | 4 | −1.2 | 1 | 4 |
| i-Bu | 3 | 2 | −0.5 | 1 | 5 |
| n-Pro | 4 | 2 | −0.2 | 0.5 | 1 |
| neohexyl | 5 | 2 | −0.3 | 1 | 2 |
| Acetoxy-ethyl | 26 | 4 | −0.5 | 1 | 2 |
| CH$_2$Ph | 6 | 2 | 0 | | |
| t-Bu | 7 | 2 | −0.7 | 0.5 | 1 |
| i-Pro | 8 | | | | |
| 2-Trimethylsilyl-1-ethyl | 9 | 4 | −1.5 | 1 | 3+ |
| n-Octyl | 10 | 2 | −3.2 | 0.5 | 3+ |
| 4-t-Butyl-benzyl | 12B | 2 | −2.2 | 0.5 | 6+ |
| n-Hexyl | 11 | 2 | −1.2 | 1 | 2 |
| 2-Propyl-1-pentyl | 13B | 2 | −2 | 1 | 6+ |
| 5-Methyl-2-hexyl | 14B | 2 | −1.5 | 1 | 4+ |
| 4-Methyl-1-pentyl | 15B | 1 | −0.8 | 1 | 2 |
| 4-Methyl-1-benzyl | 16B | 2 | −2 | 1 | 3 |
| 2,5-Dimethoxy-benzyl | 17B | 2 | −1 | 1 | 2 |
| n-Carbooctadecyl (C18) | 18B | 2 | −0.8 | 0.5 | 3 |
| 5-Carboisopropoxy-1-pentyl | 21B | 1 | −0.5 | 2 | 3 |
| 1-Carbomethoxy-1-pentyl | 22B | 1 | 0 | | |
| 1-Hydroxy-1-hexyl | 24B | 2 | −1.3 | 1 | 3 |
| exo-norbornyl | 19B | 1 | −0.7 | 0.5 | 3 |
| endo-norbornyl | 20B | 1 | −0.8 | 2 | 3 |

Pupil diameter was measured at different times after topical application of the compounds.
[a]Maximum decrease in pupil diameter.
[b]Time the maximum effect was obtained.
[c]Time when there was at least 0.5 mm decrease in pupil diameter or maximum response was maintained.

Following topical application, miosis was caused by most of the compounds indicating improvement in corneal penetration. The extent of miosis ranged from about 3% to about 50% decrease in pupil size. The duration ranged from 1 hour to longer than 6 hours (duration of the experimental period). In general, duration was related to the extent of miosis. However, there were some compounds that caused little miosis which persisted through the experimental period. This suggested a depot effect.

Compounds in which R is a 4-tert-butylbenzyl group (Example 12) or a 2-propyl-1-pentyl group (Example 13) were selected for further testing, primarily since they exhibited the desired activity essentially without the side-effects typically associated with this type of compound, such as hyperemia, swelling and discharge.

(3R, 4R)-1-carbo-(4-tert-butylbenzoxy)-3-ethyl-4-[(1-methyl-1H-imidazol-5-yl) methyl]-2-pyrrolidinone—(Ex. 12)

Effect on Pupil Size

Figure 2:
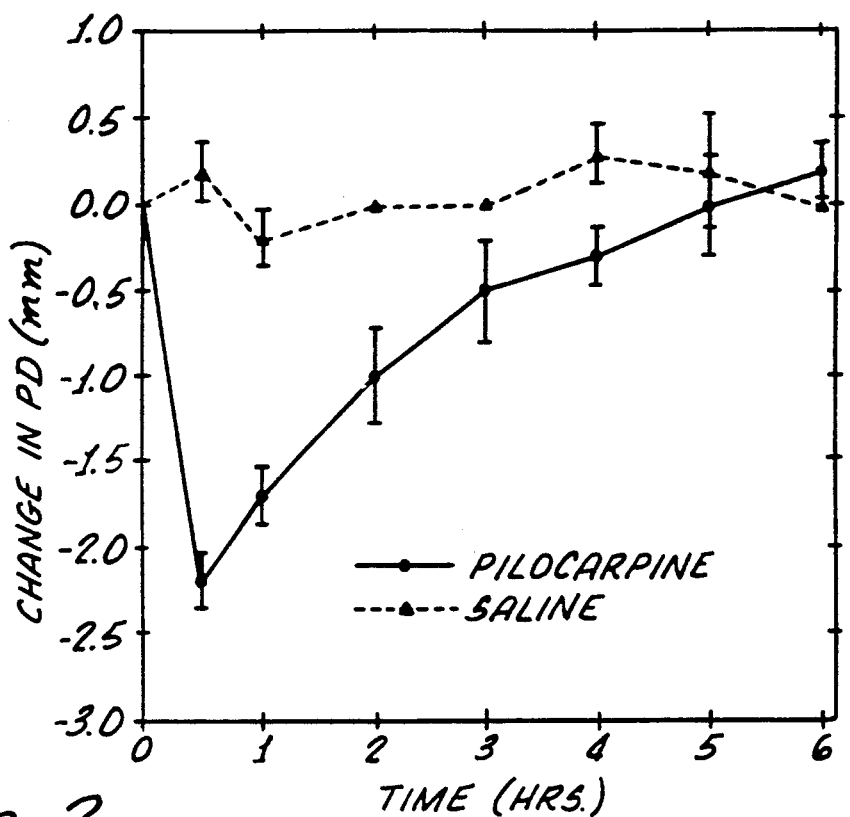
FIG. 2 illustrates the effect of a 1% pilocarpine solution on pupil diameter in rabbits.

In rabbits, the test compound caused a dose related decrease in pupil diameter. The 1% solution reached maximum activity in one hour (FIG. 1a), and the activity was equivalent to that of a 1% pilocarpine solution (FIG. 2). Since the lactam compound, according to the invention, is less potent than pilocarpine, this result suggests that its penetration was probably more than twice of the penetration of pilocarpine. The activity of the 4-tert-butylbenzoxy compound was maintained for more than 6 hours (FIG. 1a), which was longer than the duration of action of pilocarpine. The reason for this is not clear, but it can be the depot effect of the 4-tert-butylbenzoxy compound resulting in continuous generation of the lactam, and the slow hydrolysis of the lactam.

Effect on Intraocular Pressure (IOP)

Figure 1B:
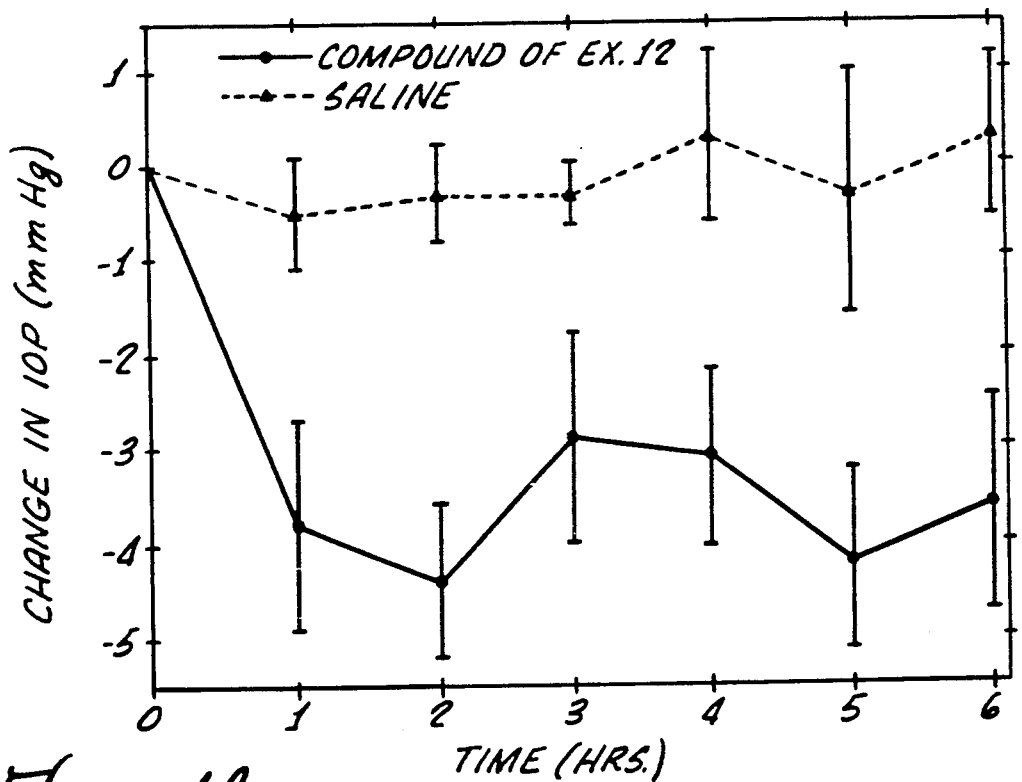
FIG. 1b shows the effect of a 1% solution of the compound of Example 12 on intraocular pressure in rabbits.

The test compound caused about a 4.5 mm Hg decrease in IOP in rabbits, 2 hours after administration. This decrease in IOP was still apparent at 6 hours (FIG. 1b). This observation was unusual because pilocarpine does not cause reduction in IOP in normotensive rabbits.

Figure 3:
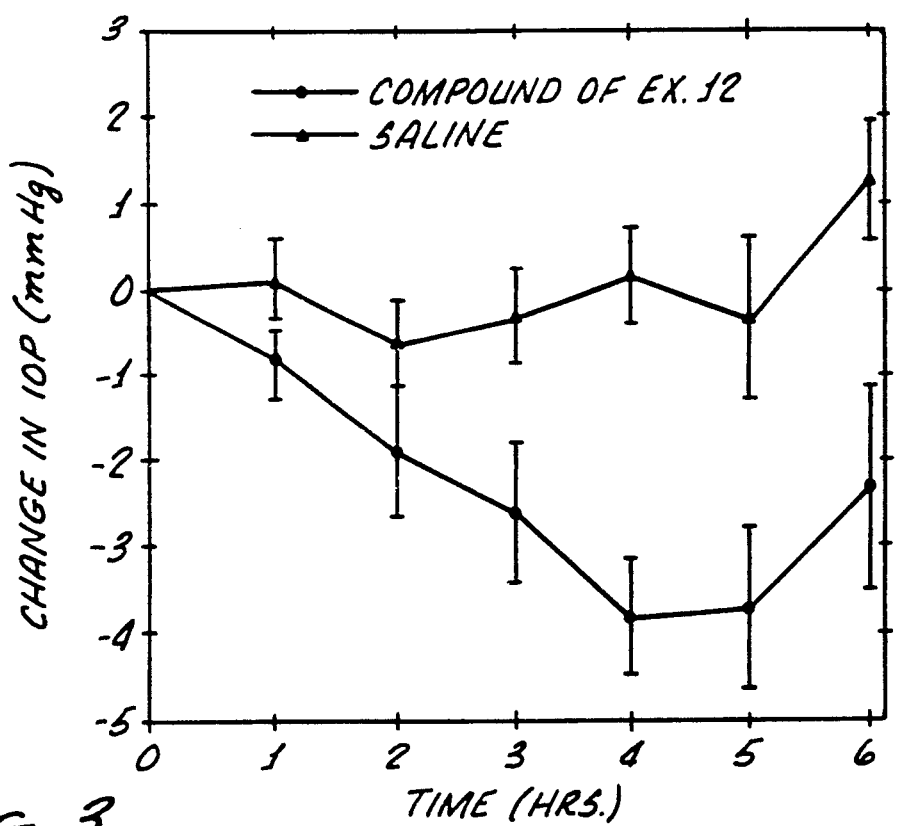
FIG. 3 shows the effect of a 0.5% solution of the compound of Example 12 on intraocular pressure in owl monkeys.

The 4-tert-butylbenzoxy test compound also reduced IOP in owl monkeys. However, the rate of response was slower, reaching maximum at 4 hours after administration (FIG. 3). This suggests slow rate of hydrolysis of the compound in the ocular tissue of the owl monkey.

(3R, 4R)-1-carbo-(2-propyl-1-pentoxy)-3-ethyl-4-[(1-methyl-1H-imidazol-5-yl) methyl]-2-pyrrolidinone—(Ex. 13)

Effect on Pupil Size

Figure 4A:
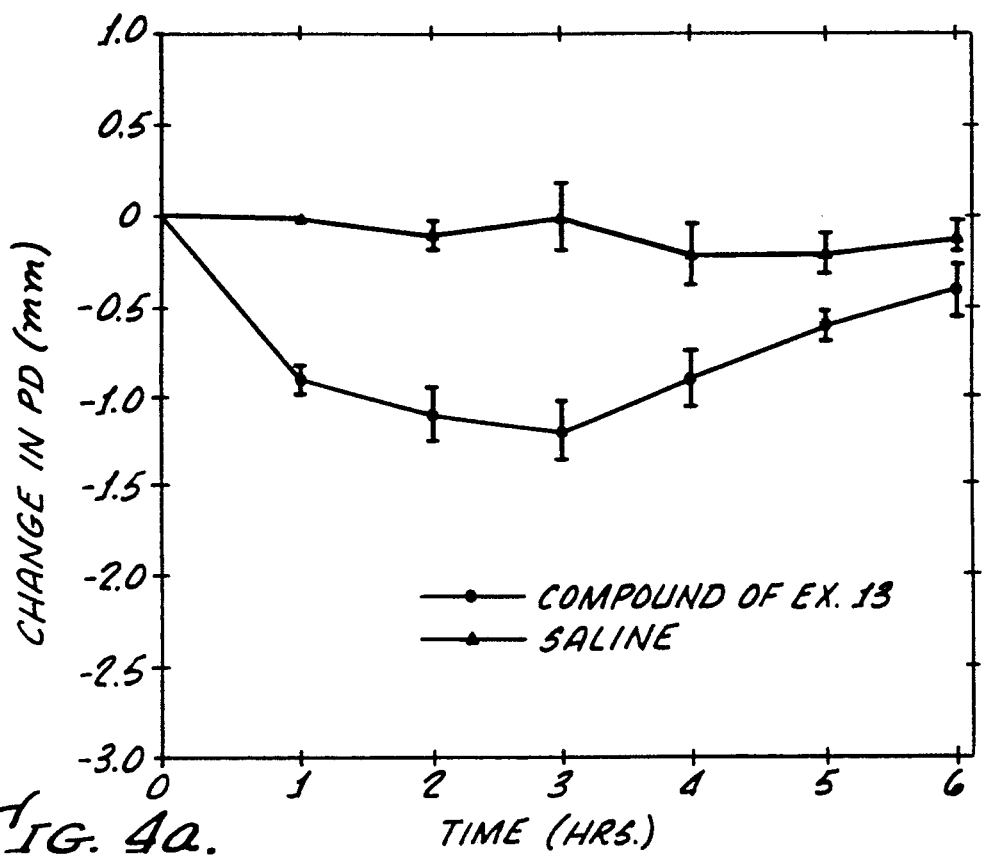
FIG. 4a illustrates the effect of a 1% solution of the compound of Example 13 on pupil diameter in rabbits.

The miotic activity of the 2-propyl-1-pentoxy test compound in rabbits was much less than that of the previously tested 4-tert-butylbenzoxy compound. Maximum effect was obtained at 3 hours and pupil size recovered gradually thereafter, but had not returned to control level at the end of the 6-hour test period (FIG. 4a).

Effect on Intraocular Pressure (IOP)

Figure 4B:
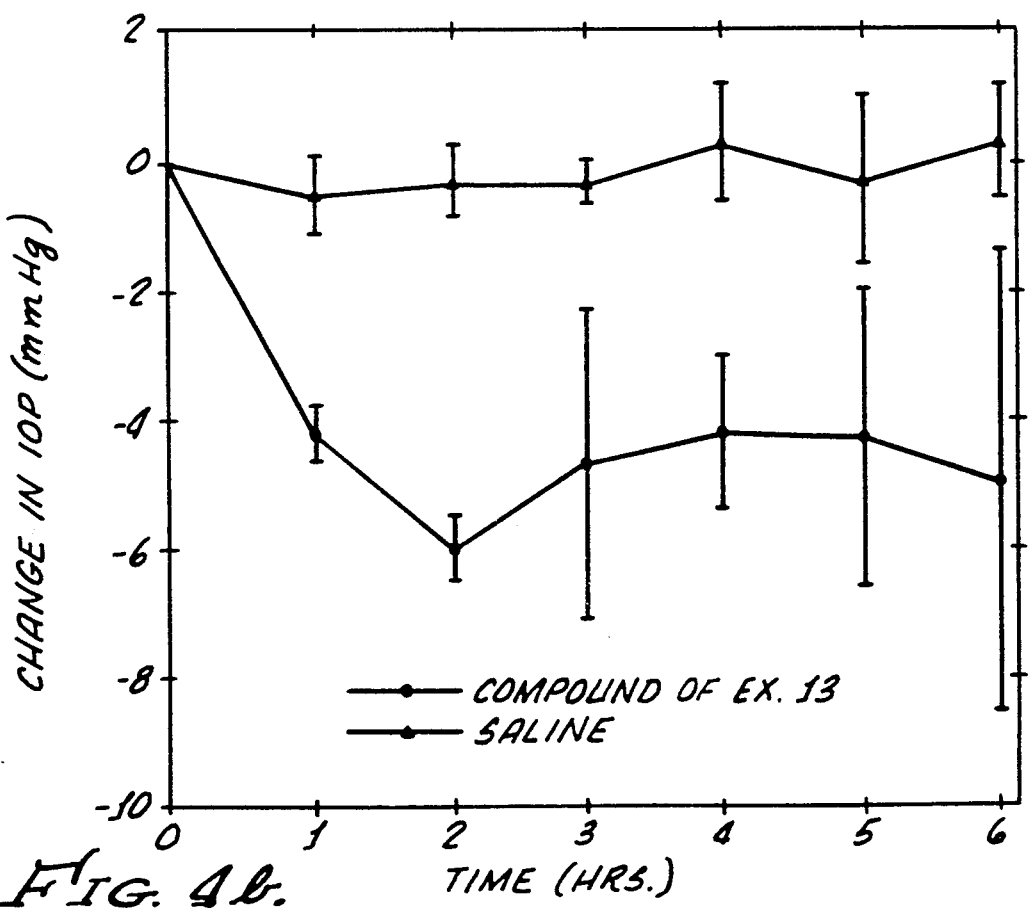
FIG. 4b illustrates the effect of a 1% solution of the compound of Example 13 on intraocular pressure in rabbits.

The 2-propyl-1-pentoxy test compound caused a 6 mm Hg decrease in IOP in rabbits (FIG. 4b). This effect was bilateral. This is a large decrease in normotensive animals. However, the IOP at time 0 was 27 mm Hg, which was high. Additional experiments are planned to confirm this observation.

EXAMPLE 1

(3R,4R)-1-carbomethoxy-3-ethyl-4[(1-methyl-1H-imidazol-5-yl)methyl]-2-pyrrolidinone (METHOD A)

To a solution of diisopropylamine (58 mg, 0.57 mmol) in tetrahydrofuran (THF) (2 mL) at 0° was added 251 μL of a 2.5 M solution of D-butyl lithium (0.63 mmol) in hexane. The solution was stirred at 0° for 15 min., then cooled to −78° and (3R, 4R)-3-ethyl-4-[(1-methyl-1H-imidazol-5-yl) methyl]-2-pyrrolidinone (118.2 mg, 0.57 mmol) in THF (2.5 mL) was added via cannula, followed by a THF (0.5 mL) rinse. After 2 hours at -78, methyl cyanoformate (50.9 mg, 0.60 mmol) was added and the reaction was maintained at −78° for 1.5 hours, then warmed to room temperature for 15 hours. The reaction was quenched with saturated aqueous NaHCO$_3$, extracted three times with CHCl$_3$, dried (Na$_2$SO$_4$), filtered, concentrated and the residue was chromatographed on silica gel (5% MeOH satured with NH$_3$/CHCl$_3$) to give 44.3 mg of (3R, 4R)-1-carbomethoxy-3-ethyl-4[(1-methyl-1H-imidazol-5-yl)methyl]-2-pyrrolidinone as an oil (28%).

$^1$H NMR (300 MHz, CDCl$_3$): 7.38 (s, 1H), 6.79 (s, 1H), 3.87 (dd, J=7.4 Hz, J=11.1 Hz, 1H), 3.80 (s, 3H), 3.54 (s, 3H), 3.34 (dd, J=6.4 Hz, J=11.1 Hz, 1H), 2.81-2.74 (m, 1H), 2.60 (dd, J=8.7 Hz, J=15.4 Hz, 1H), 2.37-2.22 (m, 2H), 1.73-1.64 (m, 2H), 0.97 (t, J=7.5 Hz, 3H). 13C NMR (75 MHz, CDCl$_3$): 174.76, 152.10, 138.18, 128.37, 127.24, 53.58, 50.53, 49.81, 34.64, 31.36, 27.96, 22.44, 11.00. High resolution mass spec. found 265.1419 for C$_{13}$H$_{19}$N$_3$O$_3$,Δ0.7 mmu.

EXAMPLE 2

(3R,4R)-1-carbobutoxy-3-ethyl-4(1-methyl-1H-imidazol-5-yl) methyl-2-pyrrolidinone The title compound was synthesized via Method A (using D-butyl chloroformate) to give 43.4 mg of (3R, 4R)-1-carbobutoxy-3-ethyl-4[(1-methyl-1H-imidazol-5-yl)methyl]-2-pyrrolidinone as an oil (19%).

$^1$H NMR (300 MHz, CDCl$_3$) 7.46 (s, 1H), 6.87 (s, 1H), 4.26 (t, J=6.5 Hz, 2H), 3.94 (dd, J=7.4 Hz, J=11.0 Hz, 1H), 3.61 (s, 3H), 3.42 (dd, J=6.5 Hz, J=11.0 Hz, 1H), 2.86 (dd, J=5.2 Hz, J=15.4 Hz, 1H), 2.67 (dd, J=9.0 Hz, J=15.5 Hz, 1H), 2.44-2.28 (m, 2H), 1.81-1.64 (m, 4H), 1.51-1.38 (m, 2H), 1.05 (t, J=7.4 Hz, 3H), 0.97 (t, J=7.4 Hz, 3H). 13C NMR (75 MHz, CDCl$_3$): 174.73, 151.50, 138.11, 128.37, 127.16, 66.53, 50.41, 49.68, 34.56, 31.28, 30.49, 27.90, 22.32, 18.93, 13.59, 10.95 High resolution mass spec. found 307.1900 for C$_{16}$H$_{25}$N$_3$O$_3$, Δ 0.4 mmu.

EXAMPLE 3

(3R,4R)-1-carboisobutoxy-3-ethyl-4[(1-methyl-1H-imidazol-5-yl) methyl]-2-pyrrolidinone To a solution of diisopropylamine (54.5 mg, 0.535 mmol) in the THF (3 mL) at 0° was added 214 μL of a 2.5 M solution of n-butyl lithium (0.535 mmol) in hexane. The solution was stirred at 0° for 15 min., then added via cannula (with a 1.0 mL THF rinse) to a solution of (3R, 4R)-3 -ethyl-4[(1-methyl-1H-imidazol-5-yl) methyl]-2-pyrrolidinone (105.8 mg, 0.51 mmol) at RT. The mixture was stirred at RT for 1 hour, then isobutyl chloroformate (73.7 mg, 0.54 mmol) was added. The solution was stirred at RT for 16 hours, quenched with saturated aqueous NaHCO$_3$, extracted three times with chloroform, dried (Na$_2$SO$_4$), filtered, concentrated and the residue was chromatographed on silica gel (5% MeOH saturated with NH$_3$/CHCl$_3$) to give 18.6 mg of (3R, 4R)-1-carboisobutoxy-3-ethyl-4[(1-methyl-1H-imidazol-5-yl) methyl]-2-pyrrolidinone as a golden oil (12%).

$^1$H NMR (300 MHz, CDCl$_3$): 7.45 (s, 1H), 6.86 (s, 1H), 4.03 (d, J=6.8 Hz, 2H), 3.94 (dd, J=7.5 Hz, J=11.1 Hz, 1H), 3.61 (s, 3H), 3.42 (dd, J=6.6 Hz, J=11.1 Hz, 1H), 2.85 (dd, J=5.3 Hz, J=15.3 Hz, 1H), 2.67 (dd, J=9.0 Hz, J=15.4 Hz, 1H), 2.44-2.28 (m, 2H), 2.11-1.94 (m, 1H), 1.81-1.70 (m, 2H), 1.04 (t, J=7.4 Hz, 3H), 0.99 (d, J=6.7 Hz, 6H). 13C NMR (75 MHz, CDCl$_3$): 174.70, 151.55, 138.14, 128.40, 127.22, 72.62, 50.45, 49.68, 34.62, 31.32, 27.96, 27.65, 22.36, 18.94, 11.00. High resolution mass spec. found 307.1902 for $C_{16}H_{25}N_3O_3$, Δ 0.6 mmu.

EXAMPLE 4

(3R, 4R)-1-carbopropoxy-3-ethyl-4[(1-methyl-1H-imidazol-5-yl) methyl-2-pyrrolidinone (METHOD B)

To a suspension of potassium hydride (23.8 mg, 0.59 mmol) in THF (5 mL) at 0° was added methanol (1.6 mg, 0.05 mmol). The mixture was allowed to stir for approximately 10 min. at 0°, then (3R, 4R)-3-ethyl-4-[(1-methyl-1H-imidazol-5-yl) methyl]-2-pyrrolidinone (99.4 mg, 0.48 mmol) in THF (1.5 mL) was added via cannula, followed by a THF (0.5 mL) rinse. The reaction was warmed to RT for 1 hour, then cooled to 0° and propyl chloroformate (73 mg, 0.60 mmol) was added dropwise. The mixture was warmed to RT and stirred for 3.5 days. The reaction was quenched with saturated aqueous $NaHCO_3$, extracted three times with $CHCl_3$, dried ($Na_2SO_4$), filtered, concentrated and the residue was chromatographed on silica gel (6% MeOH saturated with $NH_3/CHCl_3$) to give 28.6 mg of (3R, 4R)-1-carbopropoxy-3-ethyl-4[(1-methyl-1H-imidazol-5-yl)methyl]-2-pyrrolidinone as an oil (43%, adjusted for recovered starting material).

$^1$H NMR (300 MHz, $CDCl_3$): 7.44 (s, 1H), 6.84 (s, 1H), 4.19 (t, J=6.5 Hz, 2H), 3.92 (dd, J=7.4 Hz, J=11.3 Hz, 1H), 3.59 (s, 3H), 3.39 (dd, J=7.6 Hz, J=11.1 Hz, 1H), 2.83 (dd, J=5.1 Hz, J=16.2 Hz, 1H), 2.64 (dd, J=9.6 Hz, J=15.2 Hz, 1H), 2.55-2.43 (m, 2H), 1.79-1.67 (m, 4h), 1.02 (t, J=6.6 Hz, 3H), 0.99 (t, J=6.8 Hz, 3H). $^{13}$C NMR (75 MHz, $CDCl_3$): 175.01, 151.82, 138.36, 128.59, 127.42, 68.17, 50.39, 49.61, 34.58, 31.11, 27.76, 22.20, 21.70, 10.73, 9.95. High resolution mass spec. found 293.1740 for $C_5H_{23}N_3O_3$ Δ 0.1 mmu.

EXAMPLE 5

(3R,4R)-1-carbo-(3,3-dimethyl)butoxy-3-ethyl-4[(1-methyl-1H-imidazol-5-yl) methyl-2-pyrrolidinone The title compound was synthesized via Method B (using 3,3-dimethyl-1-butyl chloroformate) to give 17.0 mg of (3R, 4R)-1-carbo-(3,3-dimethyl)butoxy-3-ethyl-4[(1-methyl-1H-imidazol-5-yl) methyl]-2-pyrrolidinone as an oil (10%).

$^1$H NMR (300 MHz, $CDCl_3$): 7.45 (s, 1H), 6.85 (s, 1h), 4.30 (t, J=7.5 Hz, 2h), 3.92 (dd, J=7.4 Hz, J=11.3 Hz, 1H), 3.60 (s, 3H), 3.40 (dd, J=6.5 Hz, J=11.3 Hz, 1H), 2.82 (dd, J=6.6 Hz, J=15.7 Hz, 1H), 2.64 (dd, J=9.1 Hz, J=15.7 Hz, 1H), 2.41-2.25 (m, 2H), 1.78-1.69 (m, 2H), 1.65 (t, J=7.5 Hz, 2H), 1.03 (t, J=7.4 Hz, 3H), 0.96 (s, 9H). $^{13}$C NMR (75 MHz, $CDCl_3$): 174.98, 151.80, 138.35, 128.58, 127.45, 64.43, 50.41, 49.64, 41.51, 34.56, 31.10, 29.47, 29.30, 27.77, 22.22, 10.72. High resolution mass spec. found 335.2213 for $C_{18}H_{29}N_3O_3$, Δ 0.4 mmu.

EXAMPLE 6

(3R,4R)-1-carbobenzoxy-3-ethyl-4[(1-methyl-1H-imidazol-5-yl) methyl-2-pyrrolidinone ($R=CH_2Ph$)

This compound was synthesized via Method B (using benzyl chloroformate) to give 16.5 mg of (3R, 4R)-1-carbobenzoxy-3-ethyl-4[(1-methyl-1H-imidazol-5-yl)methyl]-2-pyrrolidinone as an oil (8.2%).

$^1$H NMR (300 MHz, $CDCl_3$): 7.45-7.31 (m, 6h), 6.82 (s, 1H), 5.30 (d, J=12.4 Hz, 1H), 5.24 (d, J=12.4 Hz, 1H), 3.92 (dd, J=7.5 Hz, J=11.1 Hz, 1H), 3.56 (s, 3H), 3.39 (dd, J=6.5 Hz, J=11.2 Hz, 1H), 2.81 (dd, J=4.9 Hz, J=15.7 Hz, 1H), 2.62 (dd, J=8.8 Hz, J=15.2 Hz, 1H), 2.41-2.25 (m, 2H), 1.78-1.68 (m, 2H), 1.01 (t, J=7.5 HZ, 3H). $^{13}$C NMR (75 MHz, $CDCl_3$): 175.02, 151.59, 138.38, 135.38, 128.75, 128.59, 128.53, 128.45, 127.47, 68.04, 50.35, 49.64, 34.60, 31.10, 27.74, 22.18, 10.73. High resolution mass spec. found 341.1733 for $C_{19}H_{23}N_3O_3$, Δ 0.6 mmu.

EXAMPLE 7

(3R,4R)-1-carbo-(2-methyl-2-propoxy)-3-ethyl-4-[(1-methyl-1H-imidazol-5-yl) methyl-2-pyrrolidinone (R=t-Bu)

This compound was synthesized via Method B (using 2-(tert-butoxy-carbonyloxyimino)-2-phenylacetonitrile) to give 135.7 mg (3R, 4R)-1-carbo-(2-methyl-2-propoxy)-3-ethyl-4-[(1-methyl-1H-imidazol-5-yl)methyl]-2-pyrrolidinone as an oil (87%).

$^H$ NMR (300 MHz, $CDCl_3$): 7.46 (s, 1H), 6.85 (s, 1H), 3.89 (dd, J=7.4 Hz, J=11.0 Hz, 1H), 3.63 (s, 3H), 3.36 (dd, J=6.6 Hz, J=11.1 Hz, 1H), 2.84 (dd, J=5.1 Hz, J=15.2 Hz, 1H), 2.66 (dd, J=8.6 Hz, J=16.2 Hz, 1H), 2.40-2.24 (m, 2H), 1.77-1.68 (m, 2H), 1.54 (s, 9H), 1.03 (t, J=7.4 Hz, 3H). $^{13}$C NMR (75 MHz, $CDCl_3$): 174.97, 149.48, 138.04, 128.48, 127.08, 82.62, 50.13, 49.45, 34.12, 30.84, 27.52, 27.43, 21.85, 10.49. High resolution mass spec. found 307.1900 for $C_{16}H_{25}N_3O_3$, Δ 0.4 mmu.

EXAMPLE 8

(3R,4R)-1-carbo-(2-propoxy)-3-ethyl-4[(1-methyl-1H-imidazol-5-yl) methyl-2-pyrrolidinone (R=i-Pro)

This compound was synthesized via Method B (using 1.0 M isopropyl chloroformate in toluene) to give 36.8 mg of (3R, 4R)-1-carbo-(2-propoxy)-3-ethyl-4[(1-methyl-1H-imidazol-5-yl) methyl]-2-pyrrolidinone as an oil (33%).

$^1$H NMR (300 MHz, $CDCl_3$): 7.37 (s, 1H), 6.78 (s, 1H), 5.03-4.96 (m, 1H), 3.83 (dd, J=7.4 Hz, J=11.1 Hz, 1H), 3.52 (s, 3H), 3.30 (dd, J=6.6 Hz, J=11.1 Hz, 1H), 2.77 (dd, J=5.1 Hz, J=15.4 Hz, 1H), 2.57 (dd, J=9.2 Hz, J=15.6 Hz, 1H), 2.33-2.17 (m, 2H), 1.71-1.61 (m, 2H), 1.25 (d, J=6.3 Hz, 6H), 0.95 (t, J=7.4 Hz, 3H). $^{13}$C NMR (75 MHz, $CDCl_3$): 175.18, 151.15, 138.33, 128.62, 127.37, 70.67, 50.35, 49.59, 34.46, 31.11, 27.73, 22.12, 21.53, 10.74. High resolution mass spec. found 293.1741 for $C_5H_{23}N_3O_3$, Δ 0.2 mmu.

EXAMPLE 9

(3R, 4R)-1-carbo-(2-trimethylsilyl-1-ethoxy)-3-ethyl-4(1-methyl-1H-imidazol-5-yl)methyl-2-pyrrolidinone (R=2-Trimethylsilyl-1-ethyl)

This compound was synthesized via Method B (using 2-trimethylsilyl-1-ethyl chloroformate) to give 21.3 mg of (3R, 4R)-1-carbo-(2-trimethylsilyl-1-ethoxy)-3-ethyl-4[(1-methyl-1H -imidazol-5-yl)methyl]-2-pyrrolidinone as an oil (14%).

$^1$H NMR (300 MHz, $CDCl_3$): 7.42 (s, 1H), 6.83 (s, 1H), 4.32 (t, J=8.7 Hz, 2H), 3.87 (dd, J=8.1 Hz, J=9.1 Hz, 1H), 3.57 (s, 3H), 3.37 (dd, J=7.1 Hz, J=11.1 Hz, 1H), 2.78 (dd, J=5.6 Hz, J=15.2 Hz, 1H), 2.61 (dd, J=10.1 Hz, J=16.2 Hz, 1H), 2.36-2.23 (m, 2H), 1.75-1.66 (m, 2H), 1.09 (m, 2H), 1.00 (t, J=7.5 Hz, 3H), 0.036 (s, 9H). $^{13}$C NMR (75 MHz, $CDCl_3$): 175.08, 151.90, 138.37, 128.62, 127.45, 65.23, 50.48, 49.66, 34.52, 31.15, 27.79, 22.25, 17.37, 10.76, 1.91. High resolution

EXAMPLE 10

(3R, 4R)-1-carbobutoxy-3-ethyl-4[(1-methyl-1H-imidazol-5-yl) methyl-2-pyrrolidinone (R=n-Octyl)

This compound was synthesized via Method B (using octyl chloroformate) to give 80.3 mg of (3R, 4R)-1-carbooctoxy-3-ethyl-4[(1-methyl-1H-imidazol-5-yl)methyl]-2-pyrrolidinone as an oil (46%).

$^1$H NMR (300 MHz, CDCl$_3$): 7.34 (s, 1H), 6.75 (s, 1H), 4.12 (m, 2H), 3.82 (dd, J=7.4 Hz, 11.1 Hz, 1H), 3.50 (s, 3H), 3.29 (dd, J=6.6 Hz, 11.1 Hz, 1H), 2.74 (dd, J=5.6 Hz, J=15.7 Hz, 1H), 2.55 (dd, J=9.1 Hz, J=15.7 Hz, 1H), 2.32–2.16 (m, 2H), 1.69–1.55 (m, 4H), 1.33–1.13 (m, 10H), 0.92 (t, J=7.5 Hz, 3H), 0.79 (t, J=6.8 Hz, 3H). $^{13}$C NMR (75 MHz, CDCl$_3$): 174.98, 151.68, 138.25, 128.50, 127.29, 66.70, 50.23, 49.51, 34.37, 31.42, 31.03, 28.79, 28.76, 28.20, 27.63, 25.36, 22.24, 22.06, 13.68, 10.62. High resolution mass spec. found 363.2519 for C$_{20}$H$_{33}$N$_3$O$_3$, Δ 0.2 mmu.

EXAMPLE 11

(3R, 4R)-1-carbohexoxy-3-ethyl-4[(1-methyl-1H-imidazol-5-yl) methyl-2-nvrrolidinone (R=n-Hexyl)

This compound was synthesized via Method B (using hexyl chloroformate) to give 51.4 mg of (3R, 4R)-1-carbohexoxy-3-ethyl-4[(1-methyl-1H-imidazol-5-yl)methyl]-2-pyrrolidinone as an oil (30%).

$^1$H NMR (300 MHz, CDCl$_3$): 7.48 (s, 1H), 6.87 (s, 1H), 4.25 (t, J=6.8 Hz, 2H), 3.94 (dd, J=7.5 Hz, J=11.0 Hz, 1H), 3.62 (s, 3H), 3.41 (dd, J=6.5 Hz, J=11.1 Hz, 1H), 2.86 (dd, J=5.1 Hz, J=15.4 Hz, 1H), 2.67 (dd, J=8.9 Hz, J=15.2 Hz, 1H), 2.45–2.27 (m, 2H), 1.83–1.67 (m, 4H), 1.47–1.28 (m, 6H), 1.02 (t, J=7.5 Hz, 3H), 0.92 (t, J=6.6 Hz, 3H). $^{13}$C NMR (75 MHz, CDCl$_3$): 174.69, 151.41, 138.04, 128.32, 127.09, 66.75, 50.34, 49.62, 34.48, 31.24, 31.19, 28.34, 27.83, 25.24, 22.32, 22.26, 13.85, 10.90. High resolution mass spec. found 335.2219 for C$_{18}$H$_{29}$N$_3$O$_3$, Δ 1.0 mmu.

EXAMPLE 12

(3R, 4R)-1-carbo-(4-tert-butylbenzoxy)-3-ethyl-4[(1-methyl-1H-imidazol-5-yl) methyl]-2-pyrrolidinone (METHOD C)

To a mixture of p-tert-butylbenzyl alcohol (329 mg, 2.0 mmol) and pyridine (158 mg, 2.0 mmol) in THF (10 mL) at ambient temperature was added 4-nitrophenyl chloroformate (402 mg, 2.0 mmol). The reaction mixture was allowed to stir at ambient temperature for 17 hours. The solvent was evaporated under vacuum, and the residue was chromatographed on silica gel (15% EtOAc/hexane) to give 403.5 mg of O-(4-nitrophenyl)-0'-(4-tert-butylbenzyl) carbonate as a white solid (61%).

$^1$H NMR (300 MHz, CDCl$_3$): δ 8.27 (d, J=9.1 Hz, 2H), 7.48–7.38 (m, 6H), 5.30 (s, 2H), 1.36 (s, 9H). $^{13}$C NMR (75 MHz, CDCl$_3$): 155.4, 152.3, 152.1, 145.2, 131.1, 128.5, 125.6, 125.1, 121.6, 70.7, 34.5, 31.1. High resolution mass spec. found 314.1027 for C$_{17}$H$_{16}$NO$_5$ (M+-CH3), Δ 0.1 mmu.

(METHOD D)

To a mixture of potassium hydride (26 mg, 0.65 mmol) and methanol (1.6 mg, 0.05 mmol) in THF (4 mL) at 0° was added (3R, 4R)-3-ethyl-4[(1-methyl-1H-imidazol-5-yl)methyl]-2-pyrrolidinone (98 mg, 0.47 mmol) in THF (1.5 mL) via cannula, followed by a THF (0.5 mL) rinse. The reaction mixture was allowed to stir at 0° for 10 mins., then ambient temperature for 1.5 hours. The reaction mixture was then cooled at 0° C., and 0-(4-nitrophenyl)-0'-(4-tert-butylbenzyl) carbonate (207 mg, 0.63 mmol) in THF (1.5 mL) was added via cannula, followed by a THF (0.5 mL) rinse. The reaction mixture was allowed to stir at 0° C. for 10 min., then ambient temperature for 18 hours. The reaction was quenched with saturated sodium bicarbonate. The solution was then extracted 3X with methylene chloride, the combined organic layers were dried (Na$_2$SO$_4$), filtered, concentrated and the residue was chromatographed on silica gel (3.5% MeOH saturated with NH$_3$/CHCl$_3$) to give 78.8 mg of (3R, 4R)-1-carbo-(4-tertbutylbenzoxy)-3-ethyl-4[(1-methyl-1H-imidazol-5-yl) methyl]-2-pyrrolidinone as a foam (42%).

$^1$H NMR (300 MHz, CDCl$_3$): 7.42–7.30 (m, 5H), 6.83 (s, 1H), 5.25 (d, J=11 Hz, 1H), 5.20 (d, J=11 Hz, 1H), 3.92 (dd, J=8.1 Hz, J=10.1 Hz, 1H), 3.57 (s, 3H), 3.38 (dd, J=6.6 Hz, J=10.1 Hz, 1H), 2.80 (dd, J=4.6 Hz, J=16.2 Hz, 1H), 2.63 (dd, J=16.2 Hz, J=8.6 Hz, 1H), 2.40–2.24 (m, 2H), 1.73 (m, 2H), 1.29 (s, 9H), 0.99 (t, J=7.6 Hz, 3H). $^{13}$C NMR (75 MHz, CDCl$_3$): 174.99, 151.60, 151.41, 138.22, 132.17, 128.44, 128.29, 127.23, 125.53, 67.75, 50.12, 49.49, 34.32, 34.27, 30.93, 27.56, 21.96, 10.60. High resolution mass spec. found 397.2366 for C$_{23}$H$_{31}$N$_3$O$_3$, Δ 0.1 mmu.

EXAMPLE 13

(3R,4R)-1-carbo-(2-propyl-1-pentoxy)-3-ethyl-4(1-methyl-1H-imidazol-5-yl) methyl-2-pyrrolidinone

A.

0-(4-nitrophenyl)-0'-(2-propyl-1-pentyl) carbonate was synthesized via Method C using 2-propyl-1-pentanol to give 397.5 mg golden oil (66%). $^1$H NMR (300 MHz, CDCl$_3$): 8.27 (d, J=9.0 Hz, 2H), 7.39 (d, J=9.3 Hz, 2H), 4.21 (d, J=5.7 Hz, 2H), 1.82–1.73 (m, 1H), 1.45–1.29 (m, 8H), 0.93 (t, J=5.7 Hz, 6H). $^{13}$C NMR (75 MHz, CDCl$_3$): 155.49, 152.50, 145.12, 125.07, 121.65, 72.10, 36.78, 33.05, 19.66, 14.14.

B.

(3R, 4R)-1-carbo-(2-propyl-1-pentoxy)-3-ethyl-4[(1-methyl-1H-imidazol-5-yl) methyl]-2-pyrrolidinone was synthesized via Method D using 0-(4-nitrophenyl)-0'-(2-propyl-1-pentyl) carbonate to give 103.0 mg oil (60%).

$^1$H NMR (300 MHz, CDCl$_3$): 7.46 (s, 1H), 6.86 (s, 1H), 4.15 (d, J=5.8 Hz, 2H), 3.94 (dd, J=7.4 Hz, J=11.0 Hz, 1H), 3.62 (s, 3H), 3.42 (dd, J=6.4 Hz, J=11.1 Hz, 1H), 2.86 (dd, J=5.2 Hz, J=15.4 Hz, 1H), 2.68 (dd, J=8.9 Hz, J=15.3 Hz, 1H), 2.43–2.28 (m, 2H), 1.82–1.69 (m, 3H), 1.43–1.28 (m, 8H), 1.04 (t, J=7.5 Hz, 3H), 0.95–0.90 (m, 6H). $^{13}$C NMR (75 MHz, CDCl$_3$): 174.58, 151.41, 137.98, 128.27, 127.04, 69.25, 50.23, 49.51, 36.54, 34.43, 33.14, 31.19, 27.77, 22.18, 19.58, 14.16, 10.84. High resolution mass spec. found 363.2537 for C$_{20}$H$_{33}$N$_3$O$_3$, Δ 1.5 mmu.

EXAMPLE 14

(3R,4R)-1-carbo(5-Methyl-2-hexoxy)-3-ethyl-4(1-methyl-1H-imidazol-5-yl) methyl-2-pyrrolidinone (METHOD E)

A.

mass spec. found 351.1980 for C$_{17}$H$_{29}$N$_3$O$_3$Si, Δ 0.2 mmu.

Method C was used to synthesize 0-(4-nitrophenyl)-0'-(5-methyl-2-hexyl) carbonate giving 421.4 mg oil (75%).

¹H NMR (300 MHz, CDCl₃): 8.25 (d, J=9.4 HZ, 2H), 7.37 (d, J=9.4 Hz, 2H), 4.89-4.79 (m, 1H), 1.78-1.50 (m, 3H), 1.35 (d, J=7.2 Hz, 3H), 1.31-1.19 (m, 2H), 0.89 (d, J=7.7 Hz, 6H). ¹³C NMR (75 MHz, CDCl₃): 155.59, 152.00, 145.12, 125.16, 121.72, 77.83, 34.14, 33.49, 27.81, 22.40, 19.66. High resolution mass spec. found 282.1334 for $C_{14}H_{20}NO_5$, Δ 0.7 mmu.

B.

(3R, 4R)-1-carbo(5-Methyl-2-hexoxy)-3-ethyl-4[(1-methyl-1H-imidazol-5-yl) methyl]-2-pyrrolidinone was synthesized via Method D using 0-(4-nitrophenyl)-0'-(5-methyl-2-hexyl) carbonate to give 95.2 mg golden oil (64%) as a mixture of diastereomers.

¹H NMR (300 MHz, CDCl₃): 7.44 (s, 1H), 6.86 (s, 1H), 4.97-4.87 (m, 1H), 3.95-3.85 (m, 1H), 3.62 (s, 3H), 3.41-3.33 (m, 1H), 2.82 (dd, J=5.3 Hz, J=15.6 Hz, 1H), 2.63 (dd, J=8.7 Hz, J=15.5 Hz, 1H), 2.38-2.24 (m, 2H), 1.77-1.62 (m, 3H), 1.58-1.47 (m, 2H), 1.29 (d, J=6.0 Hz, 3H), 1.25-1.13 (m, 2H), 1.03 (t, J=7.5 Hz, 3H), 0.87 (d, J=6.8 Hz, 6H). ¹³C NMR (75 MHz, CDCl₃): 174.69, 150.81, 150.74, 137.92, 128.27, 126.96, 74.20, 74.15, 50.18, 49.50, 34.39, 34.34, 34.09, 33.32, 31.14, 27.67, 27.57, 22.25, 22.16, 22.06, 19.67, 10.81. High resolution mass spec. found 349.2359 for $C_{19}H_{31}N_3O_3$ Δ 0.6 mmu.

EXAMPLE 15

(3R, 4R)-1-carbo-(4-methyl-1-pentoxy)-3-ethyl-4(1-methyl-1H-imidazol-5-yl) methyl-2-pyrrolidinone

A.

0-(4-nitrophenyl)-0'-(4-methyl-1-pentyl) carbonate was synthesized using Method C, except 4-nitrophenyl chloroformate was added to the mixture of 4-methyl-1-pentanol, pyridine and THF at 0., and the mixture was allowed to warm to RT overnight.

¹H NMR (300 MHz, CDCl₃): 8.31 (d, J=9.4 Hz, 2H), 7.43 (d, J=9.4 Hz, 2H), 4.32 (d, J=7.7 Hz, 2H), 1.85-1.74 (m, 2H), 1.67-1.56 (m, 1H), 1.38-1.30 (m, 2H), 0.96 (d, J=7.7 H_z, 6H). ¹³C NMR (75 MHz, CDCl₃): 155.49, 152.44, 145.18, 125.62, 121.71, 69.82, 34.52, 27.59, 26.31, 22.33. High resolution mass spec. found 268.1168 for $C_{13}H_{18}NO_5$ (MH+), Δ 1.7 mmu.

B.

(3R, 4R)-1-carbo-(4-methyl-1-pentoxy)-3-ethyl-4[(1-methyl-1H-imidazol-5-yl) methyl]-2-pyrrolidinone was synthesized via Method D using 0-(4-nitrophenyl)-0'-(4-methyl-1-pentyl) carbonate to give 71.7 mg oil (57%).

¹H NMR (300 MHz, CDCl₃): 7.43 (s, 1H), 6.86 (s, 1H), 4.21 (t, J=7.1 Hz, 2H), 3.91 (dd, J=7.4 Hz, J=11.2 Hz, 1H), 3.58 (s, 3H), 3.39 (dd, J=6.5 Hz, 11.2 Hz, 1H), 2.82 (dd, J=4.9 Hz, J=15.2 Hz, 1H), 2.64 (dd, J=9.2 Hz, J=15.2 Hz, 1H), 2.41-2.26 (m, 2H), 1.80-1.63 (m, 4H), 1.61-1.51 (m, 1H), 1.31-1.20 (m, 2H), 1.02 (t, J=7.4 Hz, 3H), 0.89 (d, J=6.5 Hz, 6H). ¹³C NMR (75 MHz, CDCl₃): 174.68, 151.36, 137.99, 128.29, 127.02, 66.96, 50.29, 49.58, 34.51, 34.42, 31.21, 27.78, 27.48, 26.26, 22.28, 22.21, 10.87. High resolution mass spec. found 335.2198 for $C_{18}H_{29}N_3O_3$, Δ 1.1 mmu.

EXAMPLE 16

(3R,4R)-1-carbo-(4-methylbenzoxy)-3-ethyl-4(1-methyl-1H-imidazol-5-yl) methyl-2-pyrrolidinone

A.

0-(4-nitrophenyl)-0'-(4-methylbenzyl) carbonate was synthesized using Method E to give 548 mg white solid (89%).

¹H NMR (300 MHz, CDCl₃): 8.26 (d, J=9.2 Hz, 2H), 7.38-7.31 (m, 4H), 7.23 (d, J=8.9 Hz, 2H), 5.25 (s, 2H), 2.36 (s, 3H).

B.

(3R, 4R)-1-carbo-(4-methylbenzoxy)-3-ethyl-4[(1-methyl-1H-imidazol-5-yl) methyl]-2-pyrrolidinone was synthesized via Method D using 0-(4-nitrophenyl)-0'-(4-methylbenzyl) carbonate to give 71.3 mg oil (47%).

¹H NMR (300 MHz, CDCl₃): 7.41 (s, 1H), 7.32 (d, J=8.1 Hz, 2H), 7.17 (d, J=8.0 Hz, 2H), 6.82 (s, 1H), 5.25 (d, J=11.8 Hz, 1H), 5.20 (d, J=12.4 Hz, 1H), 3.90 (dd, J=7.4 Hz, J=11.3 Hz, 1H), 3.56 (s, 3H), 3.38 (dd, J=6.5 Hz, J=11.1 Hz, 1H), 2.80 (dd, J=5.4 Hz, J=15.4 Hz, 1H), 2.61 (dd, J=8.9 Hz, J=15.4 Hz, 1H), 2.35 (s, 3H), 2.32-2.24 (m, 2H), 1.75-1.66 (m, 2H), 1.01 (t, J=7.5 Hz, 3H). ¹³C NMR (75 MHz, CDCl₃): 174.65, 151.08, 138.16, 137.96, 131.94, 129.06, 128.38, 128.22, 126.99, 67.84, 50.17, 49.56, 34.39, 31.15, 27.70, 22.12, 21.02, 10.81. High resolution mass spec. found 355.1883 for $C_{20}H_{25}N_3O_3$, Δ 1.3 mmu.

EXAMPLE 17

(3R, 4R)-1-carbo-(2,5-dimethoxybenzoxy)-3-ethyl-4-(1-methyl-1H-imidazol-5-yl) methyl-2-pyrrolidinone

A.

Method E was used to synthesize 0-(4-nitrophenyl)-0'-(2,5-dimethoxybenzyl) carbonate giving 518 mg pale green solid (78%).

¹H NMR (300 MHz, CDCl₃): 8.27 (d, J=9.3 Hz, 2H), 7.41 (d, J=9.3 Hz, 2H), 7.00 (d, J=2.4 Hz, 1H), 6.93-6.85 (m, 2H), 5.36 (s, 2H), 3.85 (s, 3H), 3.80 (s, 3H). ¹³C NMR (75 MHz, CDCl₃): 155.49, 153.26, 152.32, 151.70, 145.13, 125.11, 123.22, 121.65, 116.07, 114.59, 111.51, 66.36, 55.89, 55.62. High resolution mass spec. found 333.0845 for $C_{16}H_{15}NO_7$, Δ 0.4 mmu.

B.

(3R, 4R)-1-carbo-(2,5-dimethoxybenzoxy)-3-ethyl-4-[(1-methyl-1H-imidazol-5-yl) methyl]-2-pyrrolidinone was synthesized via Method D using 0-(4-nitrophenyl)-0'-(2,5-dimethoxybenzyl) carbonate to give 73.8 mg golden oil (44%).

¹H NMR (300 MHz, CDCl₃): 7.41 (s, 1H), 7.06 (s, 1H), 6.82-6.81 (m, 3H), 5.32 (d, J=13.0 Hz, 1H), 5.27 (d, J=13.1 Hz, 1H), 3.93 (dd, J=7.4 Hz, J=11.1 Hz, 1H), 3.79 (s, 3H), 3.78 (s, 3H), 3.56 (s, 3H), 3.41 (dd, J=6.3 Hz, J=11.0 Hz, 1H), 2.81 (dd, J=10.9 Hz, J=15.5 Hz, 1H), 2.63 (dd, J=9.0 Hz, J=15.4 Hz, 1H), 2.39-2.26 (m, 2H), 1.78-1.67 (m, 2H), 1.01 (t, J=7.5 Hz, 3H). ¹³C NMR (75 MHz, CDCl₃): 174.66, 153.29, 151.16, 137.99, 128.30, 127.04, 124.40, 115.05, 113.77, 111.31, 63.40, 55.85, 55.58, 50.29, 49.61, 34.46, 31.19, 27,80, 22,25, 10.88. High resolution mass spec. found 401.1966 for $C_{21}H_{27}N_3O_5$, Δ 1.5 mmu.

EXAMPLE 18

(3R,4R)-1-carbooctadecoxy-3-ethyl-4-[(1-methyl-1H-imidazol-5-yl) methyl-2-pyrrolidinone

A.

Method E was used to synthesize 0-(4-nitrophenyl)-0'-(octadecyl) carbonate giving 483 mg white solid (55%).

¹H NMR (300 MHz, CDCl₃): 8.26 (d, J=9.0 Hz, 2H), 7.38 (d, J=9.3 Hz, 2H), 4.28 (t, J=6.7 Jz, 2H), 1.75 (t,

J=6.6 Hz, 2H), 1.47-1.21 (m, 30H), 0.88 (t, J=6.3 Hz, 3H). $^{13}$C NMR (75 MHz, CDCl$_3$): 155.49, 152.38, 145.13, 125.08, 121.61, 69.49, 31.83, 29.62, 29.59, 29.47, 29.39, 29.29, 29.09, 28.39, 25.54, 22.60, 13.99. High resolution mass spec. found 436.3068 for C$_{25}$H$_{42}$NO$_5$ (MH+), Δ 0.5 mmu.

B.

(3R, 4R)-1-carbooctadecoxy-3-ethyl-4 [(1-methyl-1H-imidazol-5-yl) methyl]-2-pyrrolidinone was synthesized via Method D, using 0-(4-nitrophenyl)-0'-(octadecyl) carbonate, to give 107.6 mg golden solid (50%).

$^1$H NMR (300 MHz, CDCl$_3$): 7.42 (s, 1H), 6.84 (s, 1H), 4.21 (t, J=6.7 Hz, 2H), 3.91 (dd, J=8.2 Hz, J=11.8 Hz, 1H), 3.62 (s, 3H), 3.38 (dd, J=6.6 Hz, J=11.1 Hz, 1H), 2.81 (dd, J=5.1 Hz, J=15.3 Hz, 1H), 2.63 (dd, J=8.7 Hz, J=15.4 Hz, 1H), 2.47-2.31 (m, 2H), 1.85-1.70 (m, 4H), 1.52-1.23 (m, 30H), 1.01 (t, J=7.5 Hz, 3H), 0.88 (t, J=6.6 Hz, 3H). $^{13}$C NMR (75 MHz, CDCl$_3$): 174.62, 151.36, 137.98, 128.27, 127.06, 66.70, 50.27, 49.57, 34.44, 31.73, 31.18, 29.50, 29.39, 29.28, 29.17, 29.01, 28.36, 27.77, 25.54, 22.50 22.20, 13.95, 10.85. High resolution mass spec. found 503.4095 for C$_{30}$H$_{53}$N$_3$O$_3$, Δ 0.8 mmu.

EXAMPLE 19

(3R,4R)-1-carbo-exo-norbornoxy-3-ethyl-4-[(1-methyl-1H-imidazol-5-yl) methyl-2-pyrrolidinone

A.

0-(4-Nitrophenyl)-0'-(exo-norbornyl) carbonate was synthesized via Method E to give 425.9 mg white solid (75%).

$^1$H NMR (300 MHz, CDCl$_3$): 8.28 (d, J=9.4 Hz, 2H), 7.40 (d, J=9.4 Hz, 2H), 4.72-4.67 (m, 1H), 2.52-2.48 (m, 1H), 2.40-2.34 (m, 1H), 1.89-1.80 (m, 1H), 1.67-1.09 (m, 7H). $^{13}$C NMR (75 MHz, CDCl$_3$): 155.46, 151.68, 144.97, 124.99, 121.57, 82.83, 41.25, 38.98, 35.17, 34.96, 27.72 23.75.

B.

(3R, 4R)-1-carbo-exo-norbornoxy-3-ethyl-4-[(1-methyl-1H-imidazol-5-yl) methyl]-2-pyrrolidinone was synthesized via Method D, using 0-(4-nitrophenyl)-0'-(exo-norbornyl) carbonate, to give 98.1 mg oil (55%) as a mixture of diastereomers.

$^1$H NMR (300 MHz, DCD13): 7.43 (s, 1H), 6.84 (s, 1H), 4.72-4.66 (m, 1H), 3.88 (dd, J=6.4 Hz, J=11.1 Hz, 1H), 3.56 (s, 3H), 3.35 (dd, J=6.4 Hz, J=11.1 Hz, 1H), 2.82 (dd, J=5.1 Hz, J=15.4 Hz, 1H), 2.62 (dd, J=8.8 Hz, J=15.2 Hz, 1H), 2.42-2.33 (m, 3H), 1.80-1.67 (m, 3H), 1.63-1.47 (m, 4H), 1.22-1.09 (m, 4H), 1.01 (t, J=7.4 Hz, 3H). $^{13}$C NMR (75 MHz, CDCl$_3$): 174.61, 150.75, 137.95, 128.95, 126.97, 79.84, 50.24, 49.48, 41.18, 41.15, 39.12, 39.04, 35.11, 35.05, 34.36, 31.16, 27.82, 27.73 23.76, 22.12, 10.85. High resolution mass spec. found 345.2043 for C$_{19}$H$_{27}$N$_3$O$_3$, Δ 0.9 mmu.

EXAMPLE 20

(3R,4R)=1-carbo-endo-norbornoxy-3-ethyl-4-(1-methyl-1H-imidazol-5-yl) methyl] 2-pyrrolidinone

A.

0-(4-Nitrophenyl)-0-(endo-norbornyl) carbonate was synthesized using Method E to give 487.6 mg white solid (86%).

$^1$H NMR (300 MHz, CDCl$_3$): 8.27 (d, J=9.2 Hz, 2H), 7.40 (d, J=9.2 Hz, 2H), 5.07-4.99 (m, 1H), 2.64-2.59 (m, 1H), 2.30-2.26 (m, 1H), 2.15-2.02 (m, 1H), 1.89-1.79 (m, 1H), 1.67-1.58 (m, 1H), 1.52-1.33 (m, 4H), 1.22-1.14 (m, 1H). $^{13}$C NMR (75 MHz, CDCl$_3$); 155.79, 152.42, 145.32, 125.24, 121.80, 80.90, 39.97, 37.00, 36.26, 36.15, 28.83, 20.47.

B.

(3R, 4R)-1-carbo-endo-norbornoxy-3-ethyl-4-[(1-methyl-1H-imidazol-5-yl) methyl]2-pyrrolidinone was synthesized via Method D, using 0-(4-nitrophenyl)-0'-(endo-norbornyl) carbonate, to give 81.8 mg oil (76%) as a mixture of diastereomers.

$^1$H NMR (300 MHz, CDCl$_3$): 7.46 (s, 1H), 6.B6 (s, 1H), 5.07-5.01 (m, 1H), 3.97-3.86 (m, 1H), 3.61 (s, 3H), 3.45-3.37 (m, 1H), 2.85 (dd, J=5.4 Hz, J=15.6 Hz, 1H), 2.69 (dd, J=9.3 Hz, J=15.3 Hz, 1H), 2.56 (bs, 1H), 2.44-2.23 (m, 3H), 2.11-2.01 (m, 1H), 1.89-1.72 (m, 3H), 1.65-1.54 (m, 1H), 1.48-1.31 (m, 4H), 1.15-1.06 (m, 1H), 1.04 (t, J=7.8 Hz, 3H). $^{13}$C NMR (75 MHz, CDCl$_3$): 174.59, 151.26, 137.99, 128.30, 127.04, 78.03, 50.28, 49.49, 40.09 37.03, 36.73, 36.66, 36.25, 34.44, 34.40, 31.20, 29.05, 27.79, 22.16, 20.96, 10.90, 10.86. High resolution mass spec. found 345.2058 for C$_{16}$H$_{27}$N$_3$O$_3$, Δ 0.6 mmu.

EXAMPLE 21

(3R,4R)-1-carboxy-(5-carboisoproxy-1-pentyl)-3-ethyl-4-[(1-methyl-1H-imidazol-5-yl)methyl-2-pyrrolidinone

A.

To a solution of ε-caprolactone (1.14 g, 10.0 mmol) in H$_2$O (5 mL) at 0° was added 12.5 mL of 1 M sodium hydroxide solution (12.5 mmol). The reaction mixture was stirred at 0° for 1 h and then warmed to RT for 18 h. To the mixture, 2.5 mL of 1 M hydrochloric acid (2.5 mmol) was added, the reaction mixture was stirred at RT for 30 min, then concentrated under vacuum and dried over P$_2$O$_5$ at 1 mmHg for 4 days. Ethanol (35 mL at 60°) was added, the mixture was filtered through celite, and the precipitate was washed with ethanol. The filtrate was concentrated under vacuum, DMF (70 mL) and 2-bromopropane (1.20 g, 9.76 mmol) were added to the residue, and the mixture was stirred at RT for 24 h. Ethyl acetate was added and the mixture was washed successively with H$_2$O, 10:1 H$_2$O: saturated NaHCO$_3$, H$_2$O, then dried (Na$_2$SO$_4$), filtered, and concentrated to give 201 mg oil. After the oil was dissolved in THF (5 mL) and pyridine (137 mg, 1.73 mmol) at 0°, 4-nitrophenyl chloroformate (237.5 mg, 1.18 mmol) was added in one portion. The reaction mixture was warmed to RT for 17 h, then concentrated under vacuum. The residue was chromatographed on silica gel (25% EtOAc/hexane) to give 157.3 mg of 0-(4-nitrophenyl)-0'-(5-carboisopropoxy-1-pentyl) carbonate as an oil (4.6%).

$^1$H NMR (300 MHz, CDCl$_3$): 8.30-8.26 (m, 2H), 7.41-7.38 (m, 2H), 5.08-4.95 (m, 1H), 4.31 (t, J=7 Hz, 2H), 2.32 (t, J=8 Hz, 2H), 1.85-1.65 (m, 4H), 1.54-1.45 (m, 2H), 1.23 (d, J=7 Hz, 6H). $^{13}$C NMR (75 MHz, CDCl$_3$): 173.08, 155.72, 152.61, 145.42, 125.26, 121.80, 69.06, 67.31, 34.04 27.85, 24.81, 24.13, 21.45.

B.

(3R, 4R)-1-carboxy-(5-carboisopropoxy-1-pentyl)-3-ethyl-4-[(1-methyl-1H-imidazol-5-yl)methyl]-2-pyrrolidinone was synthesized via Method D, using 0-(4-nitrophenyl)-0'-(5-carboisopropoxy-1-pentyl) carbonate to give 86.4 mg golden oil (65%).

$^1$H NMR (300 MHz, CDCl$_3$): 7.42 (s, 1H), 6.84 (s, 1H), 5.03-4.93 (m, 1H), 4.25-4.20 (m, 2H), 3.90 (dd, J=7.4 Hz, J=11.2 Hz, 1H), 3.58 (s, 3H), 3.38 (dd, J=6.5 Hz, 11.1 Hz, 1H), 2.82 (dd, J=5.1 Hz, J=15.9

Hz, 1H), 2.64 (dd, J=9.0 Hz, J=15.3 Hz, 1H), 2.41–2.28 (m, 2H), 2.28 (t, J=7.5 Hz, 2H), 1.76–1.60 (m, 6H), 1.46–1.37 (m, 2H), 1.22 (d, J=6.3 Hz, 6H), 1.01 (t, J=7.5 Hz, 3H). $^{13}$C NMR (75 MHz, CDCl$_3$): 174.59, 172.79, 151.29, 137.96, 128.26, 126.98, 67.24, 66.28, 50.22, 49.54, 34.40, 34.20, 31.17, 28.04, 27.71, 25.06, 24.32, 22.15, 21.62, 10.80. High resolution mass spec. found 407.2407 for $C_{21}H_{33}N_3O_5$, Δ 1.3 mmu.

EXAMPLE 22

(3R,4R)-1-carboxy(1-carbomethoxy-1-pentyl)-3-ethyl-4-[(1-methyl-1H-imidazol-5-yl) methyl-2-pyrrolidinone

A.

To a solution of DL-2-hydroxycaproic acid (79.2 mg, 0.60 mmol) in dichloromethane (5 mL) at 0° was added dropwise diazomethane as a solution in diethyl ether until the yellow color persisted (approximately 4 mL). The mixture was allowed to stir at 0° for 45 min, then argon was bubbled through the solution for 5 min. The mixture was concentrated in vacuum and the residue was dissolved in THF (5 mL) and pyridine (71 mg, 0.90 mmol). After the mixture was cooled to 0., 4-nitrophenyl chloroformate (122.4 mg, 0.61 mmol) was added in one portion and the reaction was allowed to warm to RT and stirred for 18 h. The mixture was concentrated in vacuum and the residue was chromatographed on silica gel (10% EtOAc/hexane) to give 140.0 mg of 0-(4-nitrophenyl)-0'-(1-carbomethoxy-1-pentyl) carbonate as an oil (75%).

$^1$H NMR (300 MHz, CDCl$_3$): 8.31–8.28 (m, 2H), 7.45–7.42 (m, 2H), 5.06 (t, J=6.2 Hz, 1H), 3.82 (s, 3H), 2.02–1.92 (m, 2H), 1.52–1.32 (m, 4H), 0.94 (t, J=7.1 Hz, 3H). $^{13}$C NMR (75 MHz, CDCl$_3$): 170.00, 155.56, 152.27, 145.62, 125.34, 121.77, 76.45, 52.37, 30.41, 26.68, 21.84, 13.38.

B.

(3R, 4R)-1-carboxy(1-carbomethoxy-1-pentyl)-3-ethyl-4-[(1-methyl-1H-imidazol-5-yl) methyl]-2-pyrrolidinone was synthesized via Method D, using 0-(4-nitrophenyl)-0'-(-carbomethyoxy-1-pentyl) carbonate, to give 46.2 mg golden oil (40%) as a mixture of diastereomers.

$^1$H NMR (300 MHz, CDCl$_3$): 7.43 (s, 1H), 6.85 (s, 1H), 5.05 (t, J=6.4 Hz, 1H), 4.01–3.87 (m, 1H), 3.75 (s, 3H), 3.59 (s, 3H), 3.51–3.36 (m, 1H), 2.90–2.81 (m, 1H), 2.72–2.63 (m, 1H), 2.43–2.28 (m, 2H), 1.91–1.84 (m, 2H), 1.79–1.70 (m, 2H), 1.45–1.27 (m, 4H), 1.05–1.00 (m, 3H), 0.91 (t, J=7.1 Hz, 3H). $^{13}$C NMR (75 MHz, CDCl$_3$): 174.71, 170.31, 150.64, 138.08, 128.32, 128.25, 127.15, 73.94, 52.29, 50.23, 50.16, 49.56, 34.67, 31.28, 30.54, 27.79, 27.07, 27.02, 22.27, 22.13, 22.03, 13.70, 10.96, 10.91. High resolution mass spec. found 379.2096 for $C_{19}H_{29}N_3O_5$, Δ1.1 mmu.

EXAMPLE 23

(3R,4R)-1-carboxy-(5-carbo-2,5-dimethoxybenzoxy-1-pentyl)-3-ethyl-4-[(1-methyl-1H-imidazol-5-yl)methyl-2-pyrrolidinone

A.

0-(4-nitrophenyl)-0'-(5-carbo-2,5-dimethoxybenzoxy-1-pentyl) carbonate was synthesized using Method E to give 121.6 mg yellow oil (64%).

$^1$H NMR (300 MHz, CDCl$_3$): 8.27 (d, J=9.2 Hz, 2H), 7.38 (d, J=9.2 Hz, 2H), 6.91 (s, 1H), 6.82 (s, 1H), 6.81 (s, 1H), 5.16 (s, 2H), 4.29 (t, J=6.6 Hz, 2H), 3.80 (s, 3H), 3.77 (s, 3H), 2.42 (t, J=7.4 Hz, 2H), 1.83–1.69 (m, 4H), 1.55–1.43 (m, 2H). 13C NMR (75 MHz, CDCl$_3$): 173.48, 155.71, 153.59, 152.62, 145.42, 125.38, 125.28, 121.81, 115.64, 113.53, 111.52, 69.06, 61.33, 55.78, 55.47, 33.73, 27.86, 24.85, 24.13. High resolution mass spec. found 447.1526 for $C_{22}H_{25}NO_9$, Δ 0.3 mmu.

B.

(3R, 4R)-1-carboxy-(5-carbo-2,5-dimethoxybenzoxy-1-pentyl)-3-ethyl-4-[(1-methyl-1H-imidazol-5-yl)methyl]-2-pyrsolidinone was synthesized via Method D, using 0-4(nitrophenyl)-0'-(5-carbo-2,5-dimethoxybenzoxy-1-pentyl) carbonate to give 28.5 mg oil (28%).

$^1$H NMR (300 MHz, CD13): 7.43 (s, 1H), 6.90 (s, 1H), 6.84 (s, 1H), 6.823 (s, 1H), 6.818 (s, 1H), 5.13 (s, 2H), 4.22 (t, J=6.6 Hz, 2H), 3.90 (dd, J=7.4 H2, J=11.1 Hz, 1H), 3.79 (s, 3H), 3.77 (s, 3H), 3.57 (s, 3H), 3.38 (dd, J=6.5 Hz, J=11.2 Hz, 1H), 2.81 (dd, J=6.4 Hz, J=15.3 Hz, 1H), 2.63 (dd, J=9.0 Hz, J=15.4 Hz, 1H), 2.45–2.24 (m, 4H), 1.77–1.65 (m, 6H), 1.48–1.37 (m, 2H), 1.01 (t, J=7.4 Hz, 3H). $^{13}$C NMR (75 HHz, CDCl$_3$): 175.05, 173.61, 153.68, 151.83, 151.77, 138.35, 128.58, 127.42, 125.54, 115.70, 113.72, 111.64, 66.41, 61.37, 55.93, 55.63, 50.34, 49.61, 34.49, 33.89, 31.12, 28.01, 27.74, 25.07, 24.27, 22.18, 10.74. High resolution mass spec. found 516.2704 for $C_{27}H_{38}N_3O_7$, Δ 0.6 mmu.

EXAMPLE 24

(3R,4R)-1-carboxy-2-(3,4,5,6-tetrahydro-2H-pyranyl-2-oxy)
-1-hexyl-3-ethyl-4[(1-methyl-1H-imidazol-5-yl)-methyl]-2-pyrrolidinone

A.

0-(4-nitrophenyl)-0'-[2-(3,4,5,6-tetrahydro-2H-pyranyl-2-oxy)-1-hexyl]carbonate was synthesized via Method E to give 365.5 mg oil (83%).

$^1$H NMR (300 MHz, CDCl$_3$): 8.31–8.26 (m, 2H), 7.44–7.37 (m, 2H), 4.83–4.79 (m, 1H), 4.43 (dd, J=3 Hz, J=12 Hz, 1H), 4.20 (dd, J=7 Hz, J=12 Hz, 1H), 4.01–3.87 (m, 2H), 3.57–3.45 (m, 1H), 1.88–1.30 (m, 12H), 0.95 (t, J=8 Hz, 3H). $^{13}$C NMR (75 MHz, CDCl$_3$): 155.82, 152.83, 145.64, 125.46, 121.91, 97.84, 73.39, 70.35, 62.62, 31.75, 30.64, 27.36, 25.19, 22.46, 19.34, 13.69.

B.

(3R, 4R)-1-carboxy-[2-(3,4,5,6-tetrahydro-2H-pyranyl-2-oxy)-1-hexyl]-3-ethyl-4[(1-methyl-1H-imidazol-5-yl)-methyl]-2-pyrrolidinone was synthesized via Method D using 0-(4-nitrophenyl)-0'-[2-(3,4,5,6-tetrahydro-2H-pyranyl-2-oxy)-1-hexyl] carbonate, to give 144.2 mg oil (83%) as a mixture of diastereomers. To a solution of (3R, 4R)-1-carboxy -[2-(3,4,5,6,-tetrahydro-2H-pyranyl-2-oxy)-1-hexyl]-3 -ethyl-4[(1-methyl-1H-imidazol-5-yl)methyl]-2-pyrrolidinone (120.0 mg, 0.28 mmol) in dichloromethane (10 mL) at RT was added methanol (1.98 g., 61.7 mmol) and p-toluenesulfonic acid monohydrate (74.8 mg, 0.39 mmol), and the mixture was stirred at RT for 3 days. The mixture was concentrated, the residue partitioned between CH$_2$C$_{12}$ and saturated aqueous NaHCO$_3$. The aqueous layer was extracted three times with CH$_2$Cl$_2$, the combined organic fractions were dried (Na$_2$SO$_4$), filtered, concentrated, and the residue was chromatographed on silica gel (4% MeOH saturated with NH$_3$/CHCl$_3$) to give 70.7 mg of (3R, 4R)-1-carboxy -(2-hydroxy-1-hexyl)-3-ethyl-4[(1-methyl-1H-imidazol-5-yl) methyl]-2-pyrrolidinone as an oil (73%).

$^1$H NMR (300 MHz, CDCl$_3$): 7.42 (s, 1H), 6.79 (s, 1H), 4.29–4.20 (m, 1H), 4.09–4.03 (m, 1H), 3.93–3.84 (m, 2H), 3.58 (s, 3H), 3.39 (dd, J=6.6 Hz, J=11.0 Hz, 1H), 2.82 (dd, J=5.3 Hz, J=15.6 Hz, 1H), 2.64 (dd, J=8.9 Hz, J=15.3 Hz, 1H), 2.41-2.25 (m, 2H), 1.78-1.67 (m, 2H), 1.51-1.30 (m, 7H), 0.99 (t, J=7.4 Hz, 3H), 0.89 (t=7.1 Hz, 3H). $^{13}$C NMR (75 MHz, CDCl$_3$): 175.17, 151.83, 138.27, 128.46, 127.19, 70.78 70.73, 68.94, 50.26, 49.46, 34.41, 32.49, 31.08, 27.55, 27.21, 22.26, 22.03, 13.61, 10.63. High resolution mass spec. found 351.2168 for C$_{18}$H$_{29}$N$_3$O$_4$, Δ 1.0 mmu.

EXAMPLE 25

(3R, 4R)-1-carbo-(2-pivaloyl-1-hexyloxy)-3-ethyl-4(1-methyl -1H-imidazol-5-yl)methyl-2-pyrrolidinone To a solution of (3R, 4R)-1-carboxy-(2-hydroxy-1-hexyl)-3-ethyl-4[(1-methyl-1H-imidazol-5-yl)methyl]-2-pyrrolidinone (21.7 mg. 0.062 mmol) and triethylamine (9.4 mg, 0.093 mmol) in dichloromethane (2 mL) at 0 was added trimethylacetyl chloride (10.8 mg, 0.089 mmol), and the mixture was warmed to RT and stirred for 18 h. The reaction was quenched with saturated aqueous NaHCO$_3$, extracted three times with CH$_2$Cl$_2$, the combined organic extracts were dried, filtered, and concentrated. The residue was chromatographed on silica gel (2% MeOH-saturated with NH$_3$/CHCl$_3$) to give 8.4 mg of a diastereomeric mixture of (3R, 4R)-1-carbo-(2-pivaloyl-1-hexyloxy)-3-ethyl-4[(1-methyl-1H-imidazol-5-yl)methyl]-2-pyrrolidinone as an oil (31%).

$^1$H NMR (300 MHz, CDCl$_3$): 7.43 (s, 1H), 6.83 (s, 1H), 5.17-5.08 (m, 1H), 4.46-4.29 (m, 1H), 4.17-4.03 (m, 1H), 3.92-3.84 (m, 1H), 3.56 (s, 3H), 3.42-3.34 (m, 1H), 2.86-2.74 (m, 1H), 2.68-2.58 (m, 1H), 2.38-2.23 (m, 2H), 1.79-1.65 (m, 2H), 1.63-1.54 (m, 2H), 1.38-1.26 (m, 4H), 1.18 (s, 9H), 0.99 (m, 3H), 0.89 (m, 3H). $^{13}$C NMR (75 MHz, CDCl$_3$): 178.42, 178.36. 174.95, 174.89, 151.44, 151.31, 138.40, 128.60, 128.55, 127.49, 74.45, 70.85, 70.73, 67.21, 67.13, 64.45, 50.41, 50.30, 49.60, 38.66, 34.55, 31.16, 30.03, 27.84, 26.90, 22.31, 22.24, 22.14, 13.63, 10.76. High resolution mass spec. found 435.2724 for C$_{23}$H$_{37}$N$_3$O$_5$, Δ0.9 mmu.

EXAMPLE 26

(3R, 4R)-1-carbo-(1-acetoxy-1-ethoxy)-3-ethyl-4[(1-methyl-1H-imidazol-5-yl) methyl-2-pyrrolidinone and (3R, 4R)-1-acetyl-3-ethyl-4[(1-methyl-1H-imidazol-5-yl)methy]-2-pyrrolidinone To a solution of diisopropylamine (76 mg, 0.75 mmol) in THF (2.0 mL) at 0° was added 300 μL of a 2.5 M solution of n-butyl lithium (0.75 mmol) in hexane. The solution was stirred at 0° for 12 min., then (3R, 4R)-3-ethyl-4[(1-methyl -1H-imidazol-5-yl)methyl]-2-pyrrolidinone (148.0 mg, 0.71 mmol) in THF (2.0 mL) was added via cannula followed by a THF (1.0 mL) rinse, and the mixture was warmed to Rt. After 1.5 h, 0-(4-nitrophenyl)-0'-(1-acetoxy-1-ethyl) carbonate[1] (202.3 mg. 0.75 mmol) in THF (1.5 mL) was added via cannula followed by a THF (0.5 mL) rinse, and the reaction mixture was stirred at Rt for 18h. The reaction was quenched with 20:1 H$_2$O: saturated aqueous NaHCO$_3$, extracted three times with CHCl$_3$, the combined organic extracts were dried (Na$_2$SO$_4$), filtered, concentrated, and the residue was chromatographed on silica gel (3% MeOH saturated with NH$_3$/CHCl$_3$) to give 23.6 mg of a 3:1 mixture of (3R, 4R)-1-carbo-(1-acetoxy-1-ethoxy)-3-ethyl-4[(1-methyl-1H-imidazol-5-yl) methyl]-2-pyrrolidinone and (3R, 4R)-1-acetyl-3-ethyl-4[(1-methyl-1H-imidazol-5-yl) methyl]-2-pyrrolidinone as a yellow oil (10%).

[1] Alexander, J., Cargill. R., Michelson. S. R., Schwam, H., *Journal of Medicinal/Chemistry*. 31, (1988), p. 318–322.

$^1$H NMR (300 MHz, CDCl$_3$): 7.49 (s, 1H), 6.94 (s, 0.25H), 6.93 (s, 0.25H), 6.89 (s, 1H), 4.04-3.90 (m, 1H), 3.63 (s, 3H), 3.46-3.37 (m, 1H), 2.93-2.82 (m, 1H), 2.74-2.64 (m, 1H), 2.57 (s, 0.75H), 2.45-2.29 (m, 2H), 2.13 (s, 3H), 1.82-1.72 (m, 2H), 1.59 (d, J=7 Hz, 3H), 1.06 (t, J=7.5Hz, 3H). $^{13}$C NMR (75 MHz, CDCl$_3$): 174.65, 174.59, 171.12, 168.89, 149.23, 138.18, 128.28, 127.31, 127.19, 126.97, 90.27, 50.90, 50.36, 50.29, 49.57, 48.58, 34.64, 34.27, 31.33, 27.86, 27.80, 24.95, 22.27, 22.22, 20.81, 19.63, 19.50, 11.11, 10.95. High resolution mass spec. found 337.1639 for C$_{16}$H$_{23}$N$_3$O$_5$, Δ 0.1 mmu.

EXAMPLE 27

(3R, 4R)-1-carbo-[4-(4-methoxyphenyl)butyloxy1-3-ethyl-4[(1-methyl -1H-imidazol-5-yl)methyl-2-pyrrolidinone

A.

Method C was used to synthesize 0-(4-nitrophenyl)-0'-[4-(4-methoxyphenyl) butyl]carbonate giving 162.7 mg white solid (94%). $^1$H NMR (300 MHz, CDCl$_3$): 8.22 (dd, J=2.2 Hz, J=7.0 Hz, 2H), 7.37-7.32 (m, 4H), 6.90 (dd, J=2.0 Hz, J=6.7 Hz, 2H), 5.22 (s, 2H), 3.96 (t, J=6.5 Hz, 2H), 1.81-1.71 (m, 2H), 1.55-1.42 (m, 2H), 0.97 (t, J=7.4 Hz, 3H). $^{13}$C NMR (75 MHz, CDCl$_3$): 160.1, 155.8, 152.7, 145.5, 130.8, 126.2, 125.3, 121.9, 114.7, 70.9, 67.6, 31.0, 19.0, 13.5. High resolution mass spec. found 345.1210 for C$_{18}$H$_{19}$NO$_6$, Δ 0.2 mmu.

B. (cl (METHOD F)

To a solution of (3R,4R)-3-ethyl-4[(1-methyl-1H-imidazol-5-yl) methyl]-2-pyrrolidinone (77 mg, 0.37 mmol) in THF (7.0 mL) at RT was added potassium hydride (18 mg, 0.45 mmol) and methanol (1.2 mg, 0.04 mmol). The reaction mixture was stirred RT for 1h, then cooled to 0° and 0-(4-nitrophenyl)-0'-[4-(4-methoxyphenyl)butyl] carbonate (141 mg, 0.41 mmol) in THF (3.0 mL) was added dropwise. The reaction mixture was maintained at 0° for 1h, then stirred at RT for 18.5h. The reaction was quenched with 10% NaHCO$_3$. The mixture was extracted twice with EtOAc, dried (Na$_2$SO$_4$), filtered, concentrated, and the residue was chromatographed on silica gel (5% MeOH saturated with NH$_3$/CHCl$_3$) to give 105.5 mg (3R, 4R)-1-carbo-[4-(4-methoxyphenyl) butyloxy]-3-ethyl-4](1-methyl-1H-imidazol-5-yl) methyl]-2-pyrrolidinone as a nearly colorless oil (69%).

$^1$H NMR (300 MHz, CDCl$_3$): 7.42(s, 1H), 7.11-7.07 (m, 2H), 6.85-6.80 (m, 3H), 4.25-4.19 (m, 2H), 3.89 (dd, J=7.4 Hz, J=11.1 Hz, 1H), 3.78 (s, 3H), 3.57 (s, 3H), 3.37 (dd, J=6.6 Hz, J=11.1 Hz, 1H), 2.81 (dd, J=5.3 Hz, J=15.5 Hz, 1H), 2.67-2.57 (m, 3H), 2.36-2.24 (m, 2H), 1.77-1.64 (m, 4HO, 1.01 (t, J=7.4 Hz, 3H). $^{13}$C NMR (75 MHz, CDCl$_3$): 174.9, 158, 151.7, 138.3, 134.0, 129.3, 128.5, 127.3, 113.8, 66.4, 55.0, 50.2, 49.5, 34.4, 34.1, 31.0, 27.7, 27.6, 27.3, 22.1, 10.7. High resolution mass spec. found 413.2299 for C$_{23}$H$_{31}$N$_3$O$_4$, Δ 1.6 mmu.

EXAMPLE 28

(3R,4R)-1-carbo-[3-(3,4-dimethoxyphenyl)propoxy]-3-ethyl-4[(1-methyl-1H-imidazol-5-yl)methyl]-2-pyrrolidinone

A.

Method C was used to synthesize 0-(4-nitrtophenyl)-0'-[3-(3,4-dimethoxy phenyl)propyl] carbonate giving 162.3 mg near-white solid (90%). ¹H NMR (300 MHz, CDCl₃): 8.25 (e, J=9.1 Hz, 2H) 3.88 (s, 3H), 3.86 (s, 3H), 2.72 (t, J=7.6 Hz, 2H), 2.11–2.06 (m, 2H). ¹³C NMR (75 MHz, CDCl₃): 155.6, 152.6, 149, 147.5, 145.3, 135.1, 125.1, 121.6, 120.1, 111.6, 111.2, 68.4, 55.5, 55.4, 30.9, 29.7. High resolution mass spec. found 379.1496 for C₁₈H₂₃N₂O₇ (M-NH₄)⁺, Δ 0.09 mmu.

B.

(3R,4R)-1-carbo-[3-(3,4-dimethoxyphenyl)propoxy]-3-ethyl-4[(1-methyl-1H-imidazol-5-yl)methyl]-2-pyrrolidinone was synthesized via Method F using 0-(4-nitrophenyl)-0'-[3-(3,4-dimethoxyphenyl) propyl] carbonate to give 53.1 mg yellow oil (41%). ¹H NMR (300 MHz, CDCl₃): 7.43 (s, 1H), 6.83–6.72 (m, 4H), 4.25 (t, J=6.5 Hz, 2H), 3,89–3.85 (m, 1H), 3.86 (s, 3H), 3.85 (s, 3H), 3.58 (s, 3H), 3.33 (dd, J=6.6 Hz, J=11.1 Hz, 1H), 2.82 (dd, J=5.1 Hz, J=15.4 Hz, 1H), 2.68 (t, J=7.5 Hz, 2H), 2.64–2.56 (m, 1H), 2.36–2.26 (m, 2H), 2.05–2.0 (m, 2H), 1.75–1.70 (m, 2H), 1.01 (t, J=7.4 Hz, 3H). ¹³C NMR (75 MHz, CDCl₃): 174.9, 151.6, 149, 147.4, 138.2, 133.6, 128.5, 127.2, 120.3, 111.71, 111.68, 111.28, 65.8, 55.7, 55.6, 50.2, 49.5, 34.3, 31.3, 31.0, 29.8, 27.6, 22, 10.6. High resolution mass spec. found 430.2326 for C₂₃H₃₂N₃O₅, Δ 1.6 mmu.

EXAMPLE 29

Ophthalmic Preparation

The composition of a typical ophthalmic preparation according to the invention is as shown herein below:

| Ingredient | Amount (% w/v) |
| --- | --- |
| Active ingredient | 0.15 |
| Benzalkonium Chloride | 0–0.10 |
| Polyvinyl Alcohol (Grade 20-90) | 0–40 |
| Sodium Chloride | 1–10 |
| Sodium Citrate, Dihydrate | 0.01–10 |
| Citric Acid, Monohydrate | 0.01–2 |
| Purified Water | q.s. to make 100% |

I claim:

1. A racemic or optically active compound of the formula (I)

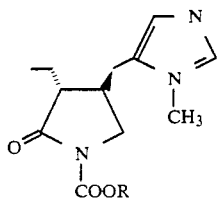

wherein R is a hydrocarbon group unsubstituted or substituted with one or more identical or different substituents selected from the group consisting of lower alkyl, lower alkoxy, (lower alkoxy)carbonyl, hydroxyl, tri(lower alkyl)silyl, phenyl(lower alkoxy)carbonyl, (lower alkyl)carbonyl, (lower alkyl)carbonyloxy, phenyl and halogen, wherein the phenyl group or moiety may be further substituted by one or more lower alkoxy groups, or a pharmaceutically acceptable acid addition salt thereof.

2. A compound according to claim 1, selected from the group consisting of:
   (3R,4R)-1-carbo-(4-tert-butylbenzoxy)-3-ethyl-4-[(1-methyl-1H-imidazol-5-yl) methyl]-2-pyrrolidinone;
   (3R,4R)-1-carbo-(2-propyl-1-pentoxy)-3-ethyl-4-[(1-methyl-1H-imidazol-5-yl) methyl]-2-pyrrolidinone,
   (3R,4R)-1-carbo-(4-methylbenzoxy)-3-ethyl-4-[(1-methyl-1H-imidazol-5-yl) methyl[-2-pyrrolidinone,
   or a pharmaceutically acceptable acid addition salt thereof.

3. Pharmaceutical composition containing a therapeutically effective amount of at least one compound defined in claim 1 as active ingredient, in admixture with conventional pharmaceutical excipient.

4. A pharmaceutical composition according to claim 3 in the form of an ophthalmic solution.

* * * * *

UNITED STATES PATENT AND TRADEMARK OFFICE
CERTIFICATE OF CORRECTION

Page 1 of 3

PATENT NO. : 5,264,449

DATED : November 23, 1993

INVENTOR(S) : Albaugh

It is certified that error appears in the above-identified patent and that said Letters Patent is hereby corrected as shown below:

Column 3, line 14; delete "R' " and insert in place thereof --R--

Column 3, line 18; delete "p" and insert in place thereof --p--

Column 3, lines 2-4; delete "U- and isopropyl, D-, sec-, iso- and tertbutyl, and isopentyl, and neo-hexyl, D- and isoheptyl, U-" and insert in place thereof --n- and isopropyl, n-, sec-, iso- and tertbutyl, n- and isopentyl, n- and neo-hexyl, n- and isoheptyl, n-

Column 3, line 67; delete "3R' " and insert in place thereof --3R--

Column 4, line 1; delete "3R' " and insert in place thereof --3R,--

Column 4, line 19; delete "suora" and insert in place thereof --supra--

Column 4, line 29; delete "D-butyl" and insert in place thereof --n-butyl--

Column 4, line 35; delete "O-p-" and insert in place thereof --O-p- --

Column 6, line 17; delete "norma" and insert in place thereof --normal--

Column 7, line 62; delete "D-butyl" and insert in place thereof --n-butyl--

Column 8, line 15; delete "13C" and insert in place thereof --$^{13}$C--

Column 8, line 25; delete "D-butyl" and insert in place thereof --n-butyl--

Column 8, line 46; delete "n-butyl" and insert in place thereof --n-butyl--

Column 9, line 36; delete "$C_5$" and insert in place thereof --$C_{15}$--

Column 10, line 47; delete "$C_5$" and insert in place thereof --$C_{15}$--

Column 10, line 51; delete "-4(1-" and insert in place thereof -- -4[(1- --

Column 10, line 52; delete "methyl-2" and insert in place thereof --methyl]-2--

Column 11, line 6; delete "carbobutoxy" and insert in place thereof --carbooctoxy--

Column 11, line 27; delete "nvrrolidinone" and insert in place thereof --pyrrolidinone--

UNITED STATES PATENT AND TRADEMARK OFFICE
CERTIFICATE OF CORRECTION

Page 2 of 3

PATENT NO. : 5,264,449
DATED : November 23, 1993
INVENTOR(S) : Albaugh

It is certified that error appears in the above-identified patent and that said Letters Patent is hereby corrected as shown below:

Column 12, line 65; delete "-4(1-" and insert in place thereof -- -4[(1- --

Column 12, line 66; delete "methyl-2" and insert in place thereof --methyl]-2--

Column 13, line 38; delete "0" and insert in place thereof --0°--

Column 15, line 68; delete "$^3$C" and insert in place thereof --$^{13}$C--

Column 16, line 9; delete "6.B6" and insert in place thereof --6.86--

Column 17, line 22; delete "0 " and insert in place thereof --0°--

Column 17, line 67; delete "13C" and insert in place thereof --$^{13}$C--

Column 17, line 68; after "152.62" insert --151.71--

Column 18, line 10; delete "CD13" and insert in place thereof --CDl$_3$--

Column 18, line 25; after "carboxy-" insert --[--

Column 18, line 27; after "hexyl" insert --]--

Column 18, line 57; delete "CH$_2$C$_{12}$" and insert in place thereof --CH$_2$Cl$_2$--

Column 19, line 12; after "ethyl-4" insert --[--

Column 19, line 13; before "-2" insert --]--

Column 19, line 18; after "0" insert --°--

Column 19, line 45; after "methyl" insert --]--

Column 19, line 51; delete "n-butyl" and insert in place thereof --$\underline{n}$-butyl--

Column 19, line 62; delete "CHC$_{13}$" and insert in place thereof --CHCl$_3$--

Column 20, line 20; before "-2" insert --]--

UNITED STATES PATENT AND TRADEMARK OFFICE
CERTIFICATE OF CORRECTION

PATENT NO. : 5,264,449
DATED : November 23, 1993
INVENTOR(S) : Albaugh

It is certified that error appears in the above-identified patent and that said Letters Patent is hereby corrected as shown below:

Column 20, line 33; delete "(cl"

Column 20, line 67; delete "nitrtophenyl" and insert in place thereof —nitrophenyl—

Column 21, line 5; delete "152.6" and insert in place thereof —152.5—

Signed and Sealed this

Twentieth Day of September, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,264,449
DATED : November 23, 1993
INVENTOR(S) : Albaugh

It is certified that error appears in the above-indentified patent and that said Letters Patent is hereby corrected as shown below:

In the abstract; delete the formula and insert in place thereof

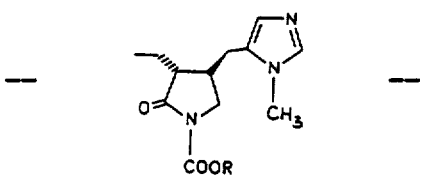

Column 2, line 5; delete the formula and insert in place thereof

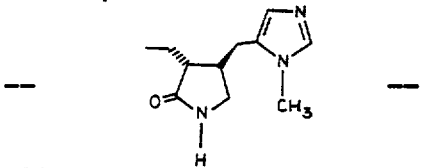

Column 22, line 10; delete the formula and insert in place thereof

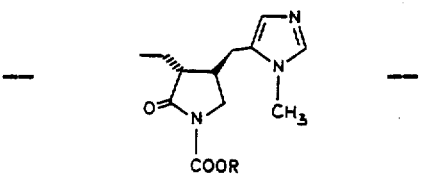

Signed and Sealed this

Twenty-second Day of November, 1994

Attest:

BRUCE LEHMAN

Attesting Officer        Commissioner of Patents and Trademarks